(12) United States Patent
Teti et al.

(10) Patent No.: US 10,450,571 B2
(45) Date of Patent: Oct. 22, 2019

(54) SMALL INTERFERING RNA (SIRNA) FOR THE THERAPY OF TYPE 2 (ADO2) AUTOSOMAL DOMINANT OSTEOPETROSIS CAUSED BY CLCN7 (ADO2 CLCN7-DEPENDENT) GENE MUTATION

(71) Applicant: Università degli Studi dell'Aquila, L'Aquila (IT)

(72) Inventors: Anna Maria Teti, L'Aquila (IT); Nadia Rucci, L'Aquila (IT); Mattia Capulli, L'Aquila (IT); Antonio Maurizi, L'Aquila (IT)

(73) Assignee: Università degli Studi dell'Aquila, L'Aquila (IT)

( * ) Notice: Subject to any disclaimer, the term of this patent is extended or adjusted under 35 U.S.C. 154(b) by 0 days.

(21) Appl. No.: 15/313,221

(22) PCT Filed: May 21, 2015

(86) PCT No.: PCT/IB2015/053730
§ 371 (c)(1),
(2) Date: Nov. 22, 2016

(87) PCT Pub. No.: WO2015/177743
PCT Pub. Date: Nov. 26, 2015

(65) Prior Publication Data
US 2017/0101644 A1    Apr. 13, 2017

(30) Foreign Application Priority Data
May 23, 2014  (IT) .............................. RM2014A0272

(51) Int. Cl.
*C07H 21/04* (2006.01)
*C12N 15/113* (2010.01)

(52) U.S. Cl.
CPC ...... *C12N 15/1138* (2013.01); *C12N 2310/14* (2013.01); *C12N 2320/34* (2013.01)

(58) Field of Classification Search
None
See application file for complete search history.

(56) References Cited

U.S. PATENT DOCUMENTS 7,820,809 B2 * 10/2010 Khvorova ............ A61K 31/713
  435/6.1
2003/0215787 A1   11/2003 Yang et al.

FOREIGN PATENT DOCUMENTS

WO    02/079414    10/2002
WO    03/062821    7/2003

OTHER PUBLICATIONS

Cho, Chong-Su. (Design and development of degradable Polyethylenimines for delivery of DNA and small interfering RNA: An updated review (2012)).*
Int'l Search Report for PCT/IB2015/053730, five pages (dated Sep. 2015).
Written Opinion of the ISA for PCT/IB2015/053730, five pages (dated Sep. 2015).
Behlke "Chemical modification of siRNAs for in vivo use" *Oligonucleotides*, vol. 18, No. 4, pp. 305-319 (Oct. 2008).
Cleiren et al. "Albers-Schonberg disease (autosomal dominant osteopetrosis, type II) results from mutations in the ClCN7 chloride channel gene" *Human Molecular Genetics*, vol. 10, No. 25, pp. 2861-2867 (Jan. 2001).
Graves et al. "The Cl−/H+ antiporter ClC-7 is the primary chloride permeation pathway in lysosomes" *Nature*, vol. 453, No. 7196, pp. 788-792 (Apr. 2008).

* cited by examiner

*Primary Examiner* — Kimberly Chong
(74) *Attorney, Agent, or Firm* — Sterne, Kessler, Goldstein & Fox P.L.L.C.

(57) ABSTRACT

The present invention lies in the field of molecules known as "small interfering RNA" with therapeutic applications. siRNAs have the ability to reduce gene expression in an extremely specific way (1). These are small sequences of double-strand RNA, normally used in laboratory to modify cell function, which revolutionized cell biology by allowing previously precluded molecular manipulations.

28 Claims, 30 Drawing Sheets

Specification includes a Sequence Listing.

| MUTATION |
| --- |
| p.G215R |
| 677-AACGGGG-684<br>A |
| p.R286W |
| 890-AAGCGGG-896<br>T |
| p.R767W |
| 2281-GCCCCAG-2287<br>A |
| p.A788D |
| 2397-TCGCCAG-2403<br>A |

Figure 2

SEQUENCE LISTING

<160> NUMBER OF SEQ ID NOS: 33

<210> SEQ ID NO 1
<211> LENGTH: 19
<212> TYPE: RNA
<213> ORGANISM: Artificial Sequence
<220> FEATURE:
<223> OTHER INFORMATION: siRNA

<400> SEQUENCE: 1
uuccucaaua gggugaaga                                              19

```
<210> SEQ ID NO 2
<211> LENGTH: 19
<212> TYPE: RNA
<213> ORGANISM: Artificial Sequence
<220> FEATURE:
<223> OTHER INFORMATION: siRNA

<400> SEQUENCE: 2
uuccucaaua ggguggaga                                                  19

<210> SEQ ID NO 3
<211> LENGTH: 19
<212> TYPE: RNA
<213> ORGANISM: Artificial Sequence
<220> FEATURE:
<223> OTHER INFORMATION: siRNA

<400> SEQUENCE: 3
uuccucaaua ggguuaaga                                                  19

<210> SEQ ID NO 4
<211> LENGTH: 18
<212> TYPE: RNA
<213> ORGANISM: Artificial Sequence
<220> FEATURE:
<223> OTHER INFORMATION: siRNA

<400> SEQUENCE: 4
uuccucaaua ggugaagg                                                   18

<210> SEQ ID NO 5
<211> LENGTH: 19
<212> TYPE: RNA
<213> ORGANISM: Artificial Sequence
<220> FEATURE:
<223> OTHER INFORMATION: siRNA

<400> SEQUENCE: 5
uuccucaaua gugugaaga                                                  19

<210> SEQ ID NO 6
<211> LENGTH: 19
<212> TYPE: RNA
<213> ORGANISM: Artificial Sequence
<220> FEATURE:
<223> OTHER INFORMATION: siRNA

<400> SEQUENCE: 6
uuccucaaua gggugacga                                                  19

<210> SEQ ID NO 7
<211> LENGTH: 19
<212> TYPE: RNA
<213> ORGANISM: Artificial Sequence
<220> FEATURE:
<223> OTHER INFORMATION: siRNA

<400> SEQUENCE: 7
uuccucaaca gggugaaua                                                  19

<210> SEQ ID NO 8
<211> LENGTH: 19
<212> TYPE: RNA
<213> ORGANISM: Artificial Sequence
<220> FEATURE:
```

<223> OTHER INFORMATION: siRNA

<400> SEQUENCE: 8
caacagagug aagaucccc                                          19

<210> SEQ ID NO 9
<211> LENGTH: 19
<212> TYPE: RNA
<213> ORGANISM: Artificial Sequence
<220> FEATURE:
<223> OTHER INFORMATION: siRNA

<400> SEQUENCE: 9
uuccucaaca gggugaaga                                          19

<210> SEQ ID NO 10
<211> LENGTH: 19
<212> TYPE: RNA
<213> ORGANISM: Artificial Sequence
<220> FEATURE:
<223> OTHER INFORMATION: siRNA

<400> SEQUENCE: 10
cucaacaggg ugaagaucc                                          19

<210> SEQ ID NO 11
<211> LENGTH: 19
<212> TYPE: RNA
<213> ORGANISM: Artificial Sequence
<220> FEATURE:
<223> OTHER INFORMATION: siRNA

<400> SEQUENCE: 11
caacagggug aagaucccc                                          19

<210> SEQ ID NO 12
<211> LENGTH: 19
<212> TYPE: RNA
<213> ORGANISM: Artificial Sequence
<220> FEATURE:
<223> OTHER INFORMATION: siRNA

<400> SEQUENCE: 12
aacagguuga agaucccc                                           19

<210> SEQ ID NO 13
<211> LENGTH: 19
<212> TYPE: RNA
<213> ORGANISM: Artificial Sequence
<220> FEATURE:
<223> OTHER INFORMATION: siRNA

<400> SEQUENCE: 13
aacaggguga agaucccc                                           19

<210> SEQ ID NO 14
<211> LENGTH: 19
<212> TYPE: RNA
<213> ORGANISM: Artificial Sequence
<220> FEATURE:
<223> OTHER INFORMATION: siRNA

<400> SEQUENCE: 14
ccugggccug uggcaccug                                          19

```
<210> SEQ ID NO 15
<211> LENGTH: 19
<212> TYPE: RNA
<213> ORGANISM: Artificial Sequence
<220> FEATURE:
<223> OTHER INFORMATION: siRNA

<400> SEQUENCE: 15
ccugggccug uggcaccuu                                                 19

<210> SEQ ID NO 16
<211> LENGTH: 19
<212> TYPE: RNA
<213> ORGANISM: Artificial Sequence
<220> FEATURE:
<223> OTHER INFORMATION: siRNA

<400> SEQUENCE: 16
ccugggccug uggcgccug                                                 19

<210> SEQ ID NO 17
<211> LENGTH: 19
<212> TYPE: RNA
<213> ORGANISM: Artificial Sequence
<220> FEATURE:
<223> OTHER INFORMATION: siRNA

<400> SEQUENCE: 17
ccugggccug uggcaucug                                                 19

<210> SEQ ID NO 18
<211> LENGTH: 19
<212> TYPE: RNA
<213> ORGANISM: Artificial Sequence
<220> FEATURE:
<223> OTHER INFORMATION: siRNA

<400> SEQUENCE: 18
acagagaagu gggacuucg                                                 19

<210> SEQ ID NO 19
<211> LENGTH: 19
<212> TYPE: RNA
<213> ORGANISM: Artificial Sequence
<220> FEATURE:
<223> OTHER INFORMATION: siRNA

<400> SEQUENCE: 19
acagagaagu gggacuucu                                                 19

<210> SEQ ID NO 20
<211> LENGTH: 19
<212> TYPE: RNA
<213> ORGANISM: Artificial Sequence
<220> FEATURE:
<223> OTHER INFORMATION: siRNA

<400> SEQUENCE: 20
acagagaagu ggggcuucg                                                 19

<210> SEQ ID NO 21
<211> LENGTH: 19
<212> TYPE: RNA
<213> ORGANISM: Artificial Sequence
<220> FEATURE:
<223> OTHER INFORMATION: siRNA
```

```
<400> SEQUENCE: 21
acagagaagu gggauuucg                                              19

<210> SEQ ID NO 22
<211> LENGTH: 19
<212> TYPE: RNA
<213> ORGANISM: Artificial Sequence
<220> FEATURE:
<223> OTHER INFORMATION: siRNA

<400> SEQUENCE: 22
aggaccucga cagguaccg                                              19

<210> SEQ ID NO 23
<211> LENGTH: 19
<212> TYPE: RNA
<213> ORGANISM: Artificial Sequence
<220> FEATURE:
<223> OTHER INFORMATION: siRNA

<400> SEQUENCE: 23
aggaccucga cagguaccu                                              19

<210> SEQ ID NO 24
<211> LENGTH: 19
<212> TYPE: RNA
<213> ORGANISM: Artificial Sequence
<220> FEATURE:
<223> OTHER INFORMATION: siRNA

<400> SEQUENCE: 24
aggaccucga caguuaccg                                              19

<210> SEQ ID NO 25
<211> LENGTH: 19
<212> TYPE: RNA
<213> ORGANISM: Artificial Sequence
<220> FEATURE:
<223> OTHER INFORMATION: siRNA

<400> SEQUENCE: 25
aggaccucga caggcaccg                                              19

<210> SEQ ID NO 26
<211> LENGTH: 19
<212> TYPE: RNA
<213> ORGANISM: Artificial Sequence
<220> FEATURE:
<223> OTHER INFORMATION: siRNA

<400> SEQUENCE: 26
aggaccucga cugguaccg                                              19

<210> SEQ ID NO 27
<211> LENGTH: 19
<212> TYPE: RNA
<213> ORGANISM: Artificial Sequence
<220> FEATURE:
<223> OTHER INFORMATION: siRNA

<400> SEQUENCE: 27
aggaccucga cagguaacg                                              19

<210> SEQ ID NO 28
<211> LENGTH: 19
```

```
<210> SEQ ID NO 28
<211> LENGTH: 19
<212> TYPE: RNA
<213> ORGANISM: Artificial Sequence
<220> FEATURE:
<223> OTHER INFORMATION: siRNA

<400> SEQUENCE: 28
aggaccucga caggucccg                                                   19

<210> SEQ ID NO 29
<211> LENGTH: 19
<212> TYPE: RNA
<213> ORGANISM: Artificial Sequence
<220> FEATURE:
<223> OTHER INFORMATION: siRNA

<400> SEQUENCE: 29
ggaacucgac agguaccgc                                                   19

<210> SEQ ID NO 30
<211> LENGTH: 19
<212> TYPE: RNA
<213> ORGANISM: Artificial Sequence
<220> FEATURE:
<223> OTHER INFORMATION: siRNA

<400> SEQUENCE: 30
aacaggguga agauccccc                                                   19

<210> SEQ ID NO 31
<211> LENGTH: 19
<212> TYPE: RNA
<213> ORGANISM: Mus musculus
<220> FEATURE:
<223> OTHER INFORMATION: siRNA WT Clcn7

<400> SEQUENCE: 31
aaugggguga agauccccc                                                   19

<210> SEQ ID NO 32
<211> LENGTH: 17
<212> TYPE: DNA
<213> ORGANISM: Artificial Sequence
<220> FEATURE:
<223> OTHER INFORMATION: primer forward

<400> SEQUENCE: 32
caagtgcttc ctcaatg                                                     17

<210> SEQ ID NO 33
<211> LENGTH: 18
<212> TYPE: DNA
<213> ORGANISM: Artificial Sequence
<220> FEATURE:
<223> OTHER INFORMATION: primer reverse

<400> SEQUENCE: 33
gccctcttcc aagctaaa                                                    18
```

SMALL INTERFERING RNA (SIRNA) FOR THE THERAPY OF TYPE 2 (ADO2) AUTOSOMAL DOMINANT OSTEOPETROSIS CAUSED BY CLCN7 (ADO2 CLCN7-DEPENDENT) GENE MUTATION

This application is the U.S. national phase of International Application No. PCT/IB2015/053730, filed May 21, 2015, which designated the U.S. and claims priority to Italian Patent Application No. RM2014A000272, filed May 23, 2014; the contents of each of which are hereby incorporated by reference.

TECHNICAL FIELD OF THE INVENTION

The present invention lies in the field of molecules known as "small interfering RNA" with therapeutic applications. siRNAs have the ability to reduce gene expression in an extremely specific way (1). These are small sequences of double-strand RNA, normally used in laboratory to modify cell function, which revolutionized cell biology by allowing previously precluded molecular manipulations.

STATE OF THE PRIOR ART

CLCN7-dependent ADO2 is a genetic condition affecting 5 individuals in 100,000 newborns (2). It generally appears in teen-aged or adult subjects (3), though various cases of infantile CLCN7-dependent ADO2 are known (4). The disease is characterized by absence of function of bone cells termed osteoclasts (5) and presents with very dense but fragile bones, hemopoiesis and senso-motory function disorders, osteomyelitis and teeth problems. Life expectancy is generally normal; yet, though rarely, early death of the affected individual can occur. Quality of life can instead be markedly compromised due to numerous atraumatic fractures, difficult to reduce surgically, and to an often severely debilitating hematological and neurological symptomatology (6). Cognitive faculties are generally preserved, though significant deficits can appear in the most severe cases (6). CLCN7-dependent ADO2 is characterized by incomplete penetrance, as only about 66% of individuals affected by the mutation manifests the disease (7). It has extremely variable severity, ranging from patients characterized by absence of symptoms to markedly compromised patients (6-8).

CLCN7-dependent ADO2 is due to a mutation of the CLCN7 gene (http://www.ncbi.nlm.nih.gov/nuccore/NM_001114331.2), comprised of 25 hexons and localized in chromosome 16 in humans and in chromosome 17 in mouse, which encodes a protein, termed ClC-7 (http://www.ncbi.nlm.nih.gov/protein/NP_001107803.1), essential to osteoclast function (5), serving for chlorine transmembrane transport. ADO2 is autosomal, as the gene resides in a nonsexual chromosome, and is dominant, as those are point mutations of a gene encoding a homodimeric protein. In point mutations, the entire protein is produced, but it exhibits a change of amino acid which modifies its function. In homodimers there are two identical subunits. Two copies of each gene exist, and in CLCN7-dependent ADO2 only one of the two genes is mutant (mutated), therefore in cells homodimers with both subunits normal, as well as heterodimers with only one subunit mutant, and homodimers with both subunits mutant are formed. Essentially, in affected individuals only one-third of the proteins functions correctly.

In patients in which the mutation determines total absence of the protein, the disease, termed recessive autosomal osteopetrosis, is much more severe because both genes are mutant (9). If instead one of the genes is not mutant, it causes production of normal protein sufficient not to let the disease develop. This condition is known as "haplosufficiency".

siRNAs (small interfering RNA) are small RNA sequences complementary to specific sequences of messenger RNA (mRNA), inducing its degradation (1). In a preceding work, the present Inventors conjectured the use of mutation-specific siRNAs to silence the expression of the mutated allele of the protein causing CLCN7-dependent ADO2 (10). Even though some siRNAs demonstrated able to block, to a certain extent, the mutated allele expression, their selectivity for the mutated allele and ability to discriminate between mutated allele and wild-type (WT) allele remains an open challenge.

Scope of the present invention is to provide novel siRNAs optimized for the treatment of CLCN7-dependent ADO2 disease.

SUMMARY OF THE INVENTION

The invention subject of the present application is based on the ascertainment, carried out by the present Inventors, that complementarity, even if total, to the sequence of mRNA comprising the point mutation is not by itself sufficient to obtain efficacious and selective siRNAs; that is to say, siRNA effective in silencing the expression of the mutated protein but inactive on the expression of the WT protein.

On the contrary, the optimum combination of efficacy and selectivity depends on plural factors, such as the mutation itself on the mRNA, the length of the sequences flanking the mutation, therefore the position of the mutated nucleotide in the siRNA sequence, the presence or absence of one or more nucleotide mismatches compared to the WT sequence of the mRNA and the position of said mismatch in the siRNA sequence: in short, from the design to the sequence itself of the siRNA.

Therefore, a first object of the present application are small interfering RNA (siRNA) and their derivatives or their precursors complementary to the region comprising a point mutation in the messenger RNA (mRNA) of the mutated human gene CLCN7. The siRNA object of the application are characterized in that (i) said mutations reflect corresponding mutations of the ClC-7 protein: Y99C, D145G, W179X, G203D, L213F, L213F, L213F, G215R, P249L, R286W, R286Q, P470Q, R409W, L490F, G677V, 688del, K689E, R762L, G765B, L766P, R767W, A788D; that (ii) the siRNAs have a nucleotide sequence comprising a fragment of 15 to 25 nucleotides, comprising the point mutation; that (iii) the siRNA selectively reduce the expression of mutated ClC-7 proteins and that (iv) the ratio of efficacy of the siRNA of the invention in reducing the expression of mutated ClC-7 protein compared to the normal protein is greater than one.

Optionally, the sequence of the small interfering RNA (siRNA) of the invention comprises, in addition to the mutated nucleotide, one or more nucleotide mismatches compared to the corresponding target sequence of the mRNA containing the mutation. Optionally, the sequence of the small interfering RNA (siRNA) of the invention also comprises a short sticky sequence to the 3' end, consisting of nucleotides dA and dT. A second object of the invention is represented by the above-indicated siRNA for use in a therapeutic treatment, specifically in the therapeutic treatment of ADO2 caused by a mutation of the CLCN7 gene.

A third object of the invention is a method for the preparation of the above-disclosed siRNAs.

A fourth object of the invention is represented by pharmaceutical compositions comprising, as active ingredient, one or more siRNAs and a pharmacologically acceptable excipient. Such compositions are preferably for parenteral administration. A further object of the invention is represented by the same compositions for use in the therapeutic treatment of ADO2, also in association with a second active ingredient.

The siRNA according to the invention, designed and tested in isolated cells and in an animal model, proved highly specific for the mutated gene. They selectively eliminate up to 95% of the transcript of the mutated gene, creating a situation, similar to haplosufficiency, which restores osteoclast function and redresses disease symptoms. The siRNA of the invention moreover afford the further advantages of being internalized by osteoclastic cells by mere incubation, with no need of any transfection agent, and of remaining in the cell for a long time.

DESCRIPTION OF THE FIGURES

FIG. 2—Construct sequences checked by direct DNA sequencing. Standard sequences are reported in the upper row, the mutated nucleotide is shown in the row below; the numbers preceding and following each sequence indicate the position of the same inside the cDNA derived from mRNA for the human CLCN7 gene (http://www.ncbi.nlm.nih.gov/nuccore/NM_001114331.2).

FIG. 15—1 month-old CD1 mice were treated with control scrambled siRNA or with 2 mg/Kg of body weight of clcn7-siRNA by TransIT-QR Hydrodynamic Delivery Kit. After 24 and 48 hours the animals were sacrificed and RNA was extracted from kidney, brain, liver, lung, heart, spleen and tibia. clcn7 gene transcriptional levels were analyzed by real-time RT-PCR, normalized for gapdh and expressed as percentage over the treatment with scrambled siRNA (point 0 on the X-axis).

(B) First cycle indentation distance (ID). (C) Touchdown distance (TDD). Mean±s.d. of 3-7 mice/group. (Student's t test).

Figure 29:
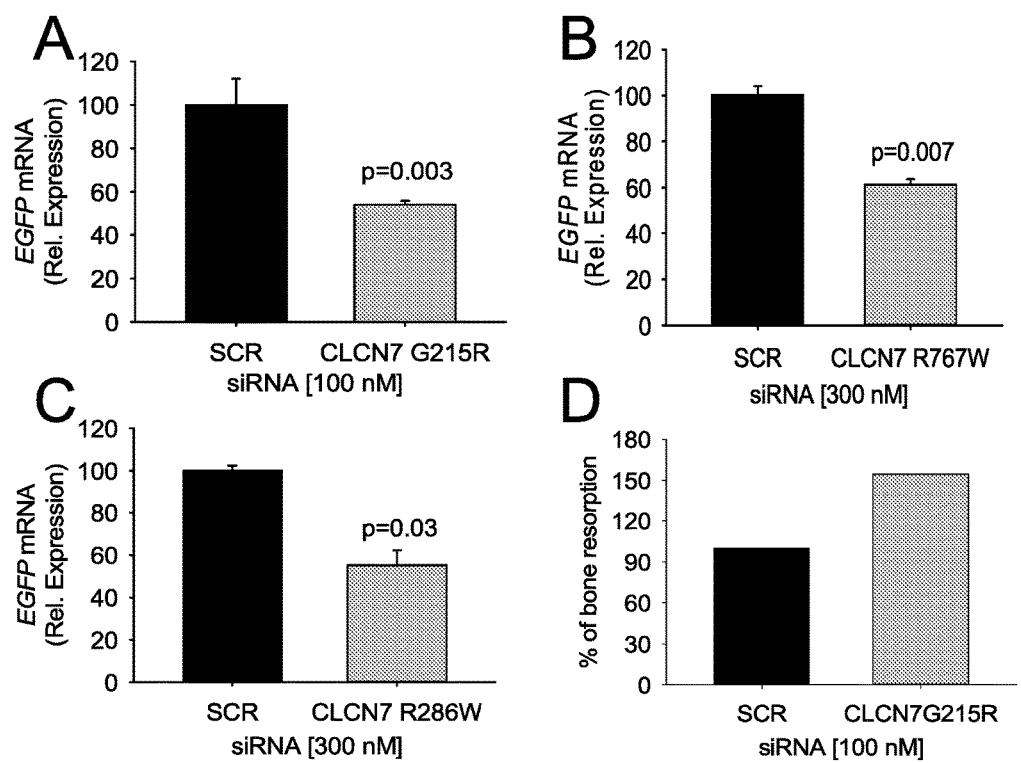

FIG. 29—Human osteoclasts were transfected with the expression vectors indicated in Figure and treated for 48 hours with the concentrations, indicated on the X-axis, of (A) p.G213R-, (B) p.R767R- and (C) p.R286W-EGFP-specific siRNAs. Real-time RT-PCR using primers specific for EGFP, normalized with GAPDH. (D) Osteoclasts were generated from blood mononuclear cells of an ADO2 patient carrying the p.G215R mutation, cultured on bovine bone slices and treated with the indicated concentration of SCR-siRNA and p.G215R-siRNA. At the end of the experiment, cells were removed by sonication and bone resorption evaluated by measuring the resorption pits. Results of a single experiment without replicates.

Figure 30:
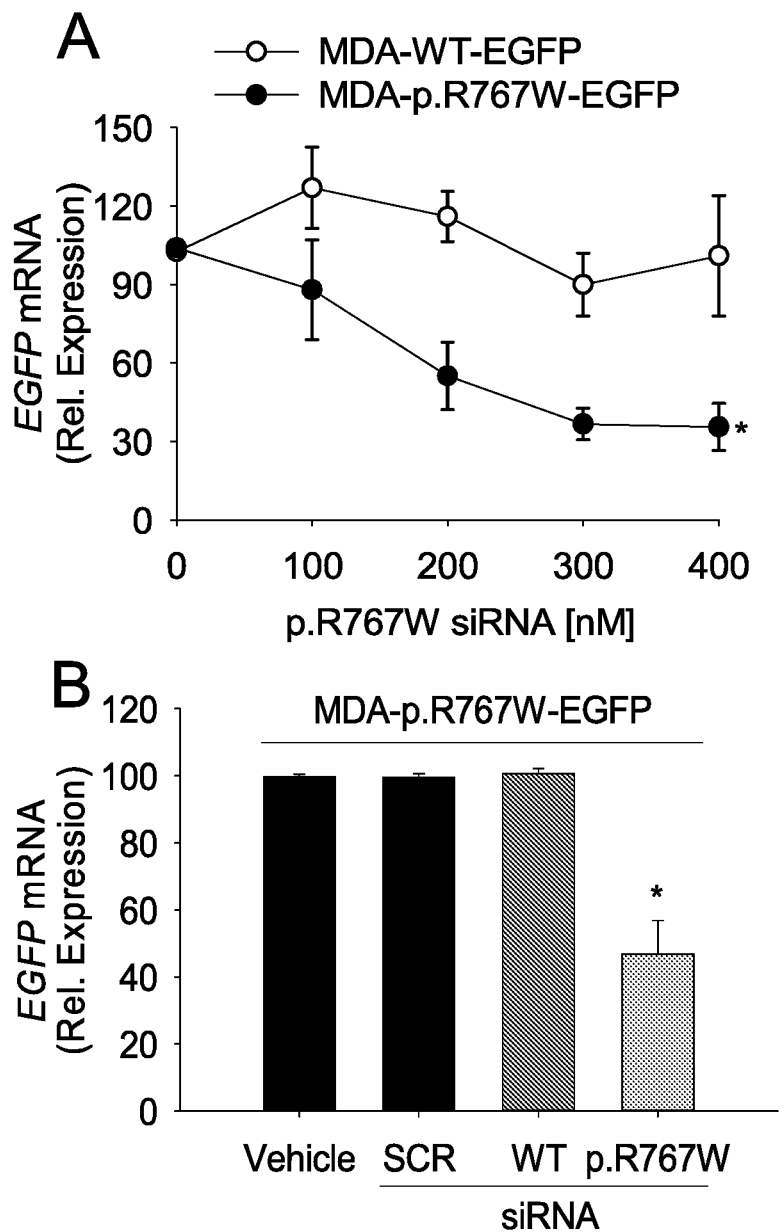

FIG. 30—(A) Human breast cancer cells MDA-MB-231 (MDA) were transfected with WT- or p.R767W-EGFP vectors and treated for 48 hours with control scrambled siRNA or with p.R767W siRNA 2C at the concentrations indicated on the X-axis. The graph shows the results of the expression of EGFP conjugated to transfected CLCN7 gene, analyzed by real-time RT-PCR performed using a pair of primers specific for EGFP normalized for GAPDH. Mean±s.e. expressed as percentage over treatment with scrambled siRNA (point 0 on the X-axis). p=0.02 (statistical test: area below curve). (B) Xenotumors were obtained by subcutaneous injection of human breast cancer cells, MDA-MB-231, transfected with p.R767W-EGFP vector, in the sides of Balb/c nu/nu athymic (immunocompromised) mice. When tumors reached the volume of 1 cm$^3$, the mice were treated once for 96 hours with vehicle (jetPEI) or 4 mg/Kg body weight of control (SCR, scrambled) siRNA, WT-siRNA or R767W siRNA 2C complexed with jetPEI. Real-time RT-PCRs were then performed on RNA extracted from the tumors, using a pair of primers specific for EGFP. Mean±s.e. normalized for GAPDH. p=0.02 (Student's t test).

DETAILED DESCRIPTION OF THE INVENTION

It is known that the mRNA of human CLCN7 gene can comprise mutations, pathogenetic ones in ADO2, which generate mutated proteins as indicated in Table 1

TABLE 1

| | Mutation and position in the protein | Amino acid substitution | Other mutation |
|---|---|---|---|
| 1 | Y99C | Tyrosine/Cysteine | |
| 2 | D145G | Aspartic acid/Glycine | |
| 3 | W179X | Tryptophan/Unknown | |
| 4 | G203D | Glycine/Aspartic acid | |
| 5 | L213F | Leucine/Phenylalanine | |
| 6 | G215R | Glycine/Arginine | |
| 7 | P249L | Proline/Leucine | |
| 8 | R286W | Arginine/Tryptophan | |
| 10 | R286Q | Arginine/Glutamine | |
| 11 | P470Q | Proline/Glutamine | |
| 12 | R409W | Arginine/Tryptophan | |
| 13 | L490F | Leucine/Phenylalanine | |
| 14 | G677V | Glycine/Valine | |
| 15 | 688del | — | Amino acid deletion in position 688 of the protein |
| 16 | K689E | Lysine/Glutamic acid | |
| 17 | R762L | Arginine/Leucine | |
| 18 | G765B | Glycine/ | |
| 19 | L766P | Leucine/Proline | |
| 20 | R767W | Arginine/Tryptophan | |

TABLE 1-continued

| | Mutation and position in the protein | Amino acid substitution | Other mutation |
|---|---|---|---|
| 21 | A788D | Alanine/Aspartic acid | |
| 22 | 2423delAG | — | Adenine/Guanine deletion in position 2423 of the DNA |

Other potential mutations of the CLCN7 gene that might result into possible muteins from the ClC-7 protein and in as many siRNAs according to the invention are the following ones: R223L, R223P, R223G, R223K, R223W, R223I, R223M, R223C, R223S, R265L, R265P, R265G, R265K, R265W, R265I, R265M, R265C, R265S, R271L, R271P, R271G, R271K, R271W, R271I, R271M, R271C, R271S, R280L, R280P, R280G, R280K, R280W, R280I, R280M, R280C, R280S, R281L, R281P, R281G, R281K, R281W, R281I, R281M, R281C, R281S, R286L, R286P, R286G, R286K, R286I, R286M, R286C, R286S, R326L, R326P, R326G, R326K, R326W, R326I, R326M, R326C, R326S, R362L, R362P, R362G, R362K, R362W, R362I, R362M, R362C, R361S, R403L, R403P, R403G, R403K, R403W, R403I, R403M, R403C, R403S, R405L, R405P, R405G, R405K, R405W, R405I, R405M, R405C, R405S, R409L, R409P, R409G, R409K, R409W, R409I, R409M, R409C, R409S, R436L, R436P, R436G, R436K, R436W, R436I, R436M, R436C, R436S, R526L, R526P, R526G, R526K, R526W, R526I, R526M, R526C, R526S, C211F, C211S, C211Y, C211R, C211G, C211W, C411F, C411S, C411Y, C411R, C411G, C411W, C438F, C438S, C438Y, C438R, C438G, C438W, W541R, W541S, W541L, W541G, W616R, W616S, W616L, W616G, L224S, L224P, L224W, L224H, L224Q, L224R, L224F, L224I, L224M, L224V, L224S, L224P, L224W, L224H, L224Q, L224R, L224F, L224I, L224M, L224V, L227S, L227P, L227W, L227H, L227Q, L227R, L227F, L227I, L227M, L227V, L564S, L564P, L564W, L564H, L564Q, L564R, L564F, L564I, L564M, L564V, S290Y, S290C, S290W, S290F, S290P, S290L, S290T, S290A, S290N, S365Y, S365C, S365W, S365F, S365P, S365L, S365T, S365A, S365N, S473Y, S473C, S473W, S473F, S473P, S473L, S473T, S473A, S473N, G241R, G241S, G241W, G241C, G241D, G241E, G241A, G241V, G347R, G347S, G347W, G347C, G347D, G347E, G347A, G347V, G361R, G361S, G361W, G361C, G361D, G361E, G361A, G361V siRNAs Small interfering RNAs complementary to the region comprising a point mutation in the messenger RNA (mRNA) of human CLCN7 gene were designed and produced for all gene mutations, known to be pathogenetic for ADO2, reported in Table 1.

The small interfering RNA (siRNA) of the invention are double-strand (duplex) sequences, of which the first one is termed "guide" (or antisense) and the second one "passenger" (or sense). The guide strand (antisense) is that complementary to the target RNA that is to be inhibited, silenced or degraded.

As the sequence of the passenger strand is complementary to the guide strand, for all siRNAs of the invention indicated in the present application, only the sequence of the guide strand is reported. The siRNAs of the invention have a sequence comprising or consisting in a fragment composed of 15 to 29 nucleotides, e.g. 16, 17, 18, 19, 20, 21, 22, 23 or 24, 25, 26, 27 or 28 nucleotides containing the point mutation;

The siRNAs of the invention are selected for their ability to selectively bind to the mRNA transcribed from the mutated allele forms of the CLCN7 gene, reducing or suppressing the expression of mutated protein ClC-7. Thanks to their selectivity of silencing of the mutated gene, their efficacy in the reduction of the expression is greater for the mutated protein than for the normal protein. Therefore, they exhibit a mutated ClC-7/normal ClC-7 ratio of efficacy greater than one.

Figure 9:
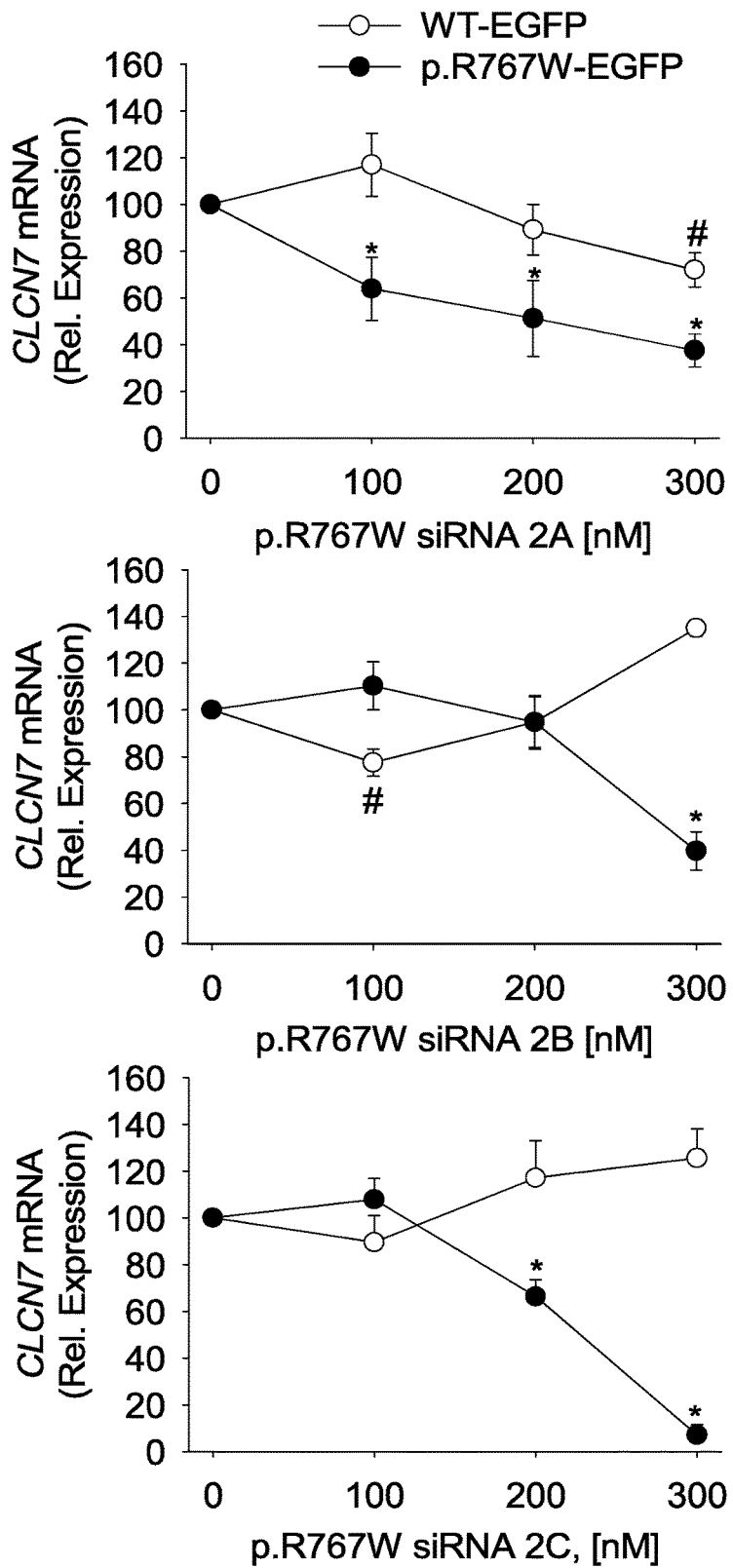
FIG. 9—HEK293 cells, transfected with WT- and p.R767W-EGFP vectors, were treated with control scrambled siRNA or with increasing concentrations of the siRNAs for p.R767W indicated in the figure (sequences in Table 2) and evaluated for CLCN7 transcript expression by real-time RT-PCR. p.R767W siRNA 2C showed greater efficacy and specificity compared with the other p.R767W siRNAs. Mean±s.e. normalized for GAPDH, expressed as percentage over the treatment with scrambled siRNA (point 0 on the X-axis). *$p<0.05$ vs. cells transfected with p.R767W-EGFP and treated with control (SCR, scrambled) siRNA. #$p<0.05$ vs. cells transfected with WT-EGFP vector and treated with control (SCR) siRNA (Student's t test).

In order to further enhance siRNAs selectivity and/or specificity to mutated mRNA, siRNAs sequence can comprise one or more nucleotides non-complementary (mismatch) to said mutated RNA sequence. With this strategy, novel siRNAs were designed (Table 2). Various siRNA exhibited significantly greater specificity for mutated mRNA, compared to W.T. mRNA. With one of them (termed p.R767W siRNA 2C), an efficacy of 90% reduction of mutated mRNA was obtained, without any reduction of WT mRNA (FIG. 9).

siRNA Derivatives

Moreover, in order to increase the stability of the same siRNAs produced and to improve the efficiency of the produced effect, one or more nucleotides forming the siRNAs sequence can be chemically modified in order to obtain derivatives of the siRNA of the invention. All derivatives described hereinafter are therefore encompassed by the protective scope of the present application.

Firstly, the siRNA sequence can be provided with a dTdT or dAdT sequence protruding to the 3' end. The latter sequence, besides lending stability and improving the efficiency, induces siRNA oligomerization in order to mimick the DNA (sticky siRNA). Sticky siRNAs can therefore be associated with usual reagents ensuring efficient siRNA distribution in vivo and decreasing the ability to cause immune responses mediated by pro-inflammatory cytokines and interferon: for instance, the jetPEI® product, which is a linear polyethylenimine derivative provided by PolyPlus Transfection.

In the in vivo assays performed on a murine ADO2 model, just the sticky siRNA/jetPEI conjugates were used. However, the siRNAs of the invention, non-modified or differently modified, as described hereinafter, can equally be used efficaciously.

Other derivatives improving the stability of the siRNAs of the invention in the form of duplex are the 2'-alcoxy (C1, C2, C3, C4) derivatives, e.g. the 2'-methoxy-derivatives, (i.e. 2'-OMe derivatives) (Denise M Kenski, Gabor Butora, Aaron T Willingham, Abby J Cooper, Wenlang Fu, Ning Qi, Ferdie Soriano, Ian W Davies and W Michael Flanagan. "siRNA-optimized Modifications for Enhanced In Vivo Activity." *Molecular Therapy Nucleic Acids* (2012) 1, e5; doi:10.1038/mtna.2011.4). 2'-OMe-derivatives, normally present in rRNA and in tRNA, are atoxic derivatives of the siRNA of the invention, wherein the —OMe group is inserted in position 2' of the ribose core in the sense- or antisense strand, or in both.

Also 2'-fluorine (i.e. 2'-F) -derivatives (Denise M. Kenski et al, supra) are compatible with the function carried out by the siRNA of the invention and enhance the stability of the duplex thereof against nuclease degradation. Fluorine incorporation in position 2' of the ribose core maintains siRNAs activity both in vitro and in vivo, increasing their stability. Combined use of 2'-F in pyrimidine nucleotides with 2'-OMe in purine nucleotides results in a duplex siRNA of extreme in-serum stability and markedly improved efficacy.

2'-O-(2-methoxyethyl) RNA derivatives (MOE-RNA) (Mark A. Behlke. "Chemical Modification of siRNAs for In Vivo Use". *Oligonucleotides* 18:305-320 (2008)) can equally be used to enhance the stability of the siRNA of the invention. MOE groups are frequently used in antisense oligonucleotides to give to the oligonucleotide high resistance to nucleases and to increase Tm.

Other siRNA derivatives, having improved function and stability, suitable to the present invention, are the 2'-O-benzyl derivatives and the 2'-O-methyl-4-pyridine (see Denise M. Kenski et al supra), 2'-amino (2'-NH), 2'-aminoethyl (2'-AE), 2'-guanidinopropyl(2'-GP) derivatives.

Particularly interesting to the ends of the present invention, due to their stability, are the LNAs (locked nucleic acids) derivatives of siRNA (see Mark A. Behlke, supra). As well-known to a person skilled in the art, these derivatives are characterized by a methylene bridge between ribose positions 2'-O and 4'-C. The methylene bridge blocks the saccharide unit into the 3'-endo configuration, thereby affording a significant Tm increase and resistance to nucleases.

Precursors

In a specific embodiment of the invention, the siRNAs or derivatives thereof can be used in the form of their precursors in vivo. The latter are also an object of the present invention.

By way of example, siRNAs can be replaced by the corresponding shRNA (short hairpin RNA), in particular in the scope of gene therapy. As is well-known to a person skilled in the art, shRNAs are short RNA sequences or transcripts, consisting in a double-strand structure formed by the coupling of two complementary sequences of about 15-29 nucleotides each, normally 19-25 or 15-20, linked by a loop of about 2-10 nucleotides, e.g. 4-9 or 5-6 nucleotides. When introduced and expressed into the cell, the shRNA-forming transcripts are processed by the enzymatic complex DICER, which by cutting the loop sequence converts, directly into the cell, the shRNAs into the corresponding siRNAs. The latter will then carry out their target gene silencing or knockdown function. Therefore, within the scope of gene therapy, the siRNAs of the invention can be replaced by the corresponding shRNAs.

All of the above-described derivatives and precursors are encompassed within the protective scope of the present application.

Within the scope of the present work, various siRNA specific for the mRNA of alleles of human CLCN7 gene containing the mutations indicated in Table 1, or the murine gene mutation p.G213R, were designed and produced. Then, the efficacy of the individual RNA fragments reported hereinafter in inhibiting the expression of protein CLC7-WT compared to proteins mutated in positions: p.G215R, p.R767W, p.R286W, p.A788D, was analyzed.

```
                            (SEQ ID NO: 1)
UUCCUCAAUAGGGUGAAGA (SEQ ID NO: 2)
UUCCUCAAUAGGGUGGAGA (SEQ ID NO: 3)
UUCCUCAAUAGGGUUAAGA (SEQ ID NO: 4)
UUCCUCAAUAGGGUGAAGG (SEQ ID NO: 5)
UUCCUCAAUAGUGUGAAGA (SEQ ID NO: 6)
UUCCUCAAUAGGGUGACGA
```

UUCCUCAACAGGGUGAA*U*A (SEQ ID NO: 7)

CAACA*G*AGUGAAGAUCCCC (SEQ ID NO: 8)

UUCCUCAACAGGGUGAAGA (SEQ ID NO: 9)

CUCAACAGGGUGAAGAUCC (SEQ ID NO: 10)

CAACAGGGUGAAGAUCCCC (SEQ ID NO: 11)

AACAGG*U*UGAAGAUCCCCC (SEQ ID NO: 12)

AACAGGGUGAAGAUCCCCC (SEQ ID NO: 13)

CCUGGGCCUGUGGCACCUG (SEQ ID NO: 14)

CCUGGGCCUGUGGCACCU*U*

(SEQ ID NO: 15)

CCUGGGCCUGUGGC*G*CCUG (SEQ ID NO: 16)

CCUGGGCCUGUGGCA*U*CUG (SEQ ID NO: 17)

ACAGAGAAGUGGGACUUCG (SEQ ID NO: 18)

ACAGAGAAGUGGGACUU*U*U (SEQ ID NO: 19)

ACAGAGAAGUGGG*G*GCUUCG (SEQ ID NO: 20)

ACAGAGAAGUGGGA*U*UUCG (SEQ ID NO: 21)

AGGACCUCGACAGGUACCG (SEQ ID NO: 22)

AGGACCUCGACAGGUACC*U*

(SEQ ID NO: 23)

AGGACCUCGACAG*U*UACCG (SEQ ID NO: 24)

AGGACCUCGACAGG*C*ACCG (SEQ ID NO: 25)

AGGACCUCGAC*U*GGUACCG (SEQ ID NO: 26)

AGGACCUCGACAGGUAACG (SEQ ID NO: 27)

AGGACCUCGACAGGU*C*CCG (SEQ ID NO: 28)

GGAACUCGACAGGUACCGC (SEQ ID NO: 29)

In the experimental work described in the present application, all siRNA sequences reported above were equipped with a dTdT sequence protruding to the 3' end to improve their stability and efficacy. For in vivo use, the dTdT sequence is replaced by the dAdT sequence, which further improves the stability and efficacy thereof and enables the binding thereof to any vehicle allowing an improved in vivo distribution of the siRNA and reducing any immune response.

The results obtained with the siRNAs assayed in vitro, in terms of their efficacy on WT mRNA or on mutated mRNA, are listed in Table 2 below.

TABLE 2

| Mutation | siRNA name | Number of mismatches vs wild-type | 5' sense-sequence | Efficacy vs wild-type | Efficacy vs Mutant |
|---|---|---|---|---|---|
| p.G215R | G215R 1M | 2 | UUCCUCAA*U*AGGGUGAAGA-dTdT 3' | + | 0 |
| | G215R 2A | 3 | UUCCUCAA*U*AGGGUG*G*AGA-dTdT 3' | + | 0 |
| | G215R 2B | 3 | UUCCUCAA*U*AGGGU*U*AAGA-dTdT 3' | ++ | 0 |
| | G215R 2C | 3 | UUCCUCAA*U*AGGGUGAAG*G*-dTdT 3' | +++ | 0 |
| | G215R 2D | 3 | UUCCUCAA*U*AG*U*GUGAAGA-dTdT 3' | 0 | ND* |
| | G215R 2E | 3 | UUCCUCAA*U*AGGGUGA*C*GA-dTdT 3' | 0 | ND* |
| | G215R 2F | 2 | UUCCUCAACAGGGUGAA*U*A-dTdT 3' | ++ | + |
| | G215R 2G | 2 | CAACA*G*AGUGAAGAUCCCC-dTdT 3' | ++ | ++ |
| | G215R 2H | 1 | UUCCUCAACAGGGUGAAGA-dTdT 3' | + | + |
| | G215R 2I | 1 | CUCAACAGGGUGAAGAUCC-dTdT 3' | ++ | + |
| | G215R 2L | 1 | CAACAGGGUGAAGAUCCCC-dTdT 3' | + | ++ |
| | G215R 2N | 2 | AACAGG*U*UGAAGAUCCCCC-dTdT 3' | ++ | + |
| | G215R 2M | 1 | AACAGGGUGAAGAUCCCCC-dTdT 3' | 0 | +++ |

TABLE 2-continued

| Mutation | siRNA name | Number of mismatches vs wild-type | 5' sense-sequence | Efficacy vs wild-type | Efficacy vs Mutant |
|---|---|---|---|---|---|
| p.R767W | R767W 1 | 1 | CCUGGGCCUGUGGCACCUG-dTdT 3' | ++ | ++ |
| | R767W 2A | 2 | CCUGGGCCUGUGGCACCUU-dTdT 3' | + | ++ |
| | R767W 2B | 2 | CCUGGGCCUGUGGCGCCUG-dTdT 3' | + | +++ |
| | R767W 2C | 2 | CCUGGGCCUGUGGCAUCUG-dTdT 3' | 0 | ++++ |
| p.R286W | R286W 1 | 1 | ACAGAGAAGUGGGACUUCG-dTdT 3' | +++ | ++ |
| | R286W 2A | 2 | ACAGAGAAGUGGGACUUCU-dTdT 3' | + | ++ |
| | R286W 2B | 2 | ACAGAGAAGUGGGGCUUCG-dTdT 3' | 0 | ++ |
| | R286W 2C | 2 | ACAGAGAAGUGGGAUUUCG-dTdT 3' | + | ++++ |
| p.A788D | A788D 1 | 1 | AGGACCUCGACAGGUACCG-dTdT 3' | ++++ | +++ |
| | A788D 2A | 2 | AGGACCUCGACAGGUACCU-dTdT 3' | ++++ | +++ |
| | A788D 2B | 2 | AGGACCUCGACAGUUACCG-dTdT 3' | ++++ | +++ |
| | A788D 2C | 2 | AGGACCUCGACAGGCACCG-dTdT 3' | ++++ | +++ |
| | A788D 2D | 2 | AGGACCUCGACUGGUACCG-dTdT 3' | ++++ | ++ |
| | A788D 2E | 2 | AGGACCUCGACAGGUAACG-dTdT 3' | ++++ | ++ |
| | A788D 2F | 2 | AGGACCUCGACAGGUCCCG-dTdT 3' | 0 | 0 |
| | A788D 2G | 2 | GGAACUCGACAGGUACCGC-dTdT 3' | 0 | + |

The sequences of siRNAs used in the in vitro study report in bold underlined the mutant nucleotide (referred to human sequence http://www.ncbi.nlm.nih.gov/nuccore/NM_001114331.2) and in bold italics the additional mismatch nucleotide/s. siRNAs indicated in bold in the second column are those deemed most effective and specific. The assays were performed in HEK293 human cells, apart from siRNAs marked with (*), assayed exclusively in human WT osteoclasts, whose efficacy on the corresponding transcript was not determined (ND). Also a siRNA recognizing the mRNA of CLCN7 gene (http://www.ncbi.nlm.nih.gov/nuccore/NM_011930.3) was produced, mutated in position 213 of mouse protein (p.G213R) (corresponding to mutation p.G215R in humans) as indicated in Table 3.

siRNA sequence for gene p.G213R-clcn7 and for the normal gene (clcn7) to be used in vivo. Bold underlined=mutant nucleotide; Bold italics=mismatch nucleotide.

The preferred siRNAs of the invention are:

CAACAAGGGUGAAGAUCCCC (SEQ ID NO: 11)

AACAGGGUGAAGAUCCCCC (SEQ ID NO: 13)

CCUGGGCCUGUUGGCACCUU (SEQ ID NO: 15)

CCUGGGCCUGUGGCGCCUG (SEQ ID NO: 16)

TABLE 3

| siRNA | siRNA name | Number of mismatches vs wild-type | 5' sense sequence |
|---|---|---|---|
| p.G213R | p.G213R-clcn7 | 2 | AACAGGGUGAAGAUCCCCCdAdT3' (SEQ ID NO: 30) |
| WT | clcn7 | 0 | AAUGGGGUGAAGAUCCCCCdAdT3' (SEQ ID NO: 31) |

-continued

CCUGGGCCUCUGGCAUCUG (SEQ ID NO: 17)

ACAGAGAACUGGGACUUCU (SEQ ID NO: 19)

ACAGAGAACUGGGGCUUCG (SEQ ID NO: 20)

ACAGAGAACUGGGAUUUCG (SEQ ID NO: 21)

GGAAACUCGACAGGUACCGC (SEQ ID NO: 29)]

In a preferred embodiment of the invention, all of the above-listed siRNAs are provided, for in vivo use, with the short dAdT sequence protruding to the 3' end.

Method for the Preparation of the siRNAs

Nucleotide synthesis methods for the preparation of short RNA sequences are known to a person skilled in the art and described in the state of the prior art. The siRNAs of the invention were produced by chemical synthesis, and are represented by duplexes of small oligonucleotides. These are comprised of 19 ribonucleotides with 2 deoxyribonucleotide "overhangs" at the 3' end. Post-synthesis, the siRNAs were subjected to the following purification processes:

Salts removal by ethanol precipitation, or using C 18-type chromatography columns Removal of 2'-ACE group present in RNA bases Pairing with the antisense sequence (synthesized in a separate reaction).

Purification 1: the siRNA duplex is purified by acrylamide gel electrophoresis

Purification 2: the siRNA duplex, obtained by the above-described step, is further purified with ion-exchange liquid chromatography (HPLC)

Purification 3: the siRNA duplex, obtained by the above-described step, is subjected to counterionic exchange (Na$^+$), desalted, sterilized by filtration and tested for presence of endotoxins.

Compositions and Dosages

The siRNAs of the invention, their chemical derivatives and/or precursors can be administered systemically or locally.

Figure 10:
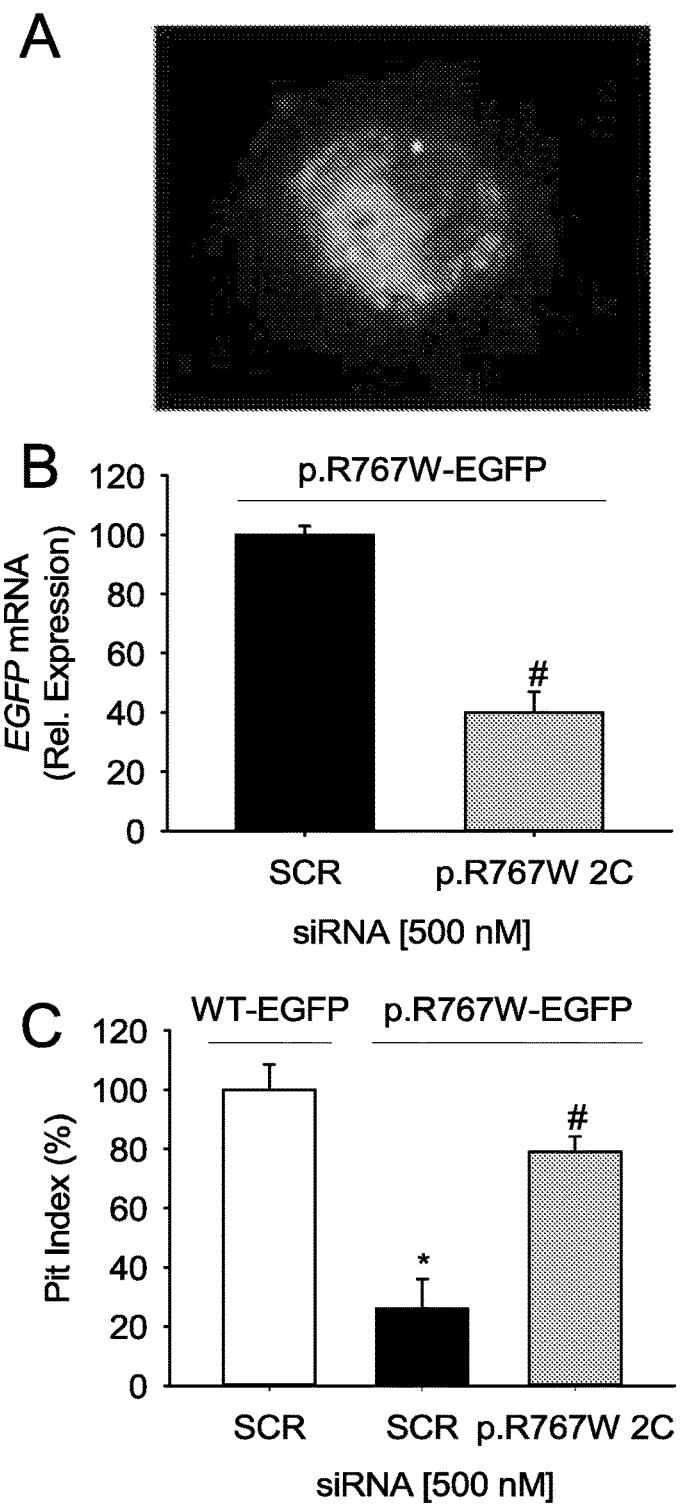
FIG. 10—(A) Human osteoclasts were differentiated from peripheral blood mononuclear cells of a healthy donor and incubated with 300 nM Cy3-CLCN7 WT siRNA for 48 hours. Cells were then fixed with 4% paraformaldehyde and Cy3 fluorescence inside osteoclasts was detected by confocal microscopy. Objective lens magnification=63X. (B,C) Human osteoclasts were transfected with empty vector or with p.R767W-EGFP vector. Osteoclasts transfected with p.R767W-EGFP vector were treated for 48 hours with control (SCR) siRNA or p.R767W siRNA 2C (Table 2) at the indicated concentrations. After 48 hours, expression (B) of the EGFP transcript normalized for GAPDH, and (C) bone resorption were analyzed, respectively by real-time RT-PCR and pit assay. Mean±s.e. #$p<0.005$ vs. osteoclasts transfected with p.R767W-EGFP and treated with control (SCR) siRNA. *$p<0.05$ vs. osteoclasts transfected with empty EGFP vector (Student's t test).

Tests conducted in vitro on cell cultures and in vivo on animal model demonstrated that the siRNAs of the invention are effectively internalized in the cell with no need of any transfection agent, rather by mere incubation with the cell in solution. In fact, the incubation, under standard cell culture conditions, of osteoclasts differentiated from peripheral blood mononuclear cells of healthy donors with siRNA of the invention or derivatives thereof highlighted siRNA incorporation into the cell and its preservation up to +7 days after treatment (FIG. 10).

Therefore, pharmaceutical compositions suitable to the administration of the siRNAs of the invention or of their chemical derivatives are compositions containing a pharmaceutically effective amount of siRNA, its derivative or its precursor, in a suitable, essentially liquid excipient. Such compositions are in the form of solutions, suspensions or emulsions. Any pharmaceutical excipient suitable for such applications can therefore be used. Suitable excipients are physiological solutions for parenteral use, hydroalcoholic solutions, glycol solutions, water/oil or oil/water emulsions, liposome or exosome emulsions/suspensions, oily solutions, micellar suspensions, vesicles, or complexes with PEI (polyethyleneimine) or complexes with atelocollagen, all containing the usual pharmaceutical additives, diluents, stabilizers and pH adjusters to physiological values.

Administration of the siRNA of the invention, derivatives or precursors thereof, can occur parenterally, e.g., the intravenous, intraperitoneal, intramuscular, intradermal, subcutaneous, intraosseus, intracartilagineous, intraarticular administration. Alternatively, the administration can be carried out orally, through pills, tablets, formulations for buccal or sublingual dissolution, capsules, soft capsules, films, powders, granulate; rectally or vaginally, through suppositories or ovules; by inhalation, e.g. intrabronchial.

Local administration can occur through any formulation suitable for local application, e.g. through topical application or direct application on or in the tissues to be treated, or again by local administration of a siRNA precursor and in situ production of the siRNA of the invention. Compositions based on exosomes, liposomes, vesicles, micelles containing the siRNA or their precursors are useful to attain both a systemic and a local effect.

To obtain a local effect, the siRNAs of the invention or their derivatives or precursors can be administered through viral or nonviral vectors, or through the DNA encoding the siRNAs, or as isolated (naked) RNA (Pelled et al., 2010 Tissue Engineering: Part B, Volume 16, No. 1, 13-20) or through three-dimensional biocompatible matrices or implants, based, e.g., on fibrinogen and thrombin polymers and located in the application point.

In a specific embodiment, the siRNAs or their derivatives or precursors are bound or associated or complexed to usual reagents ensuring an effective in vivo distribution of the siRNA, for instance polyethyleneimine (PEI) or derivatives thereof, such as the polyethyleneimine-polyethylene glycol-N-acetylgalactosamine (PEI-PEG-GAL) complex, or the polyethyleneimine-polyethylene glycol-tri-N-acetyl galactosamine (PEI-PEG-triGAL) complex. In a specific embodiment of the invention, the siRNAs are bound to the jetPEI® product, which is a linear derivative of polyethyeneimine provided by PolyPlus Transfection.

Alternatively, the siRNAs of the invention can be locally administered in the form of their shRNA precursor within the scope of a gene therapy. For instance, a shRNA, or the DNA encoding a shRNA, can be transferred into a mammalian cell, by using, e.g., a suitable plasmid or an adenoviral vector as described by Egermann et al., *Human Gene Ther*. May 2006; 17 (5):507-17. The shRNAs expressed and processed by the cell itself produce the corresponding siRNAs able to silence the target gene.

In an in vivo form of administration alternative to the vectors, the siRNAs can be transferred into a cell through electroporation, ultrasoundporation, cationic liposome-mediated transfection, microinjection, electropulsation.

In another alternative form of local administration, the siRNAs of the invention, their derivatives or precursors, can be bound, adsorbed, immobilized even through covalent bonding to a matrix able to release the genetic material (gene-activated matrix (GAM)) as described by Luginbuehl et al., 2004, Eur J Pharm Biopharm 58:197-208, and then implanted in the zone of interest as described by Fang et al., 1996 (Proc Natl Acad Sci USA 93, 5753).

Transfection agents, though not necessary, can however be used to improve siRNA internalization into osteoclasts. Transfection agents suitable for the present invention are: lipofectamine, nucleofection by Amaxa Nucleofector® (Lonza, Cologne, Germany) method using a specific kit (Cat# VPA-1007, Lonza).

Posology

Moreover, in vitro and in vivo tests conducted within the scope of the present invention demonstrated that the siRNAs internalized in the cell, i.e. in the osteoclasts, preserve their integrity and therefore their functionality over a period of several days.

Hence, the treatment regimen with siRNAs of the invention provides administrations from once a day to once a week, e.g. 1, 2, 3, 4, 5, 6 or 7 administrations/week. Alternatively, the treatment can be carried out with a daily administration, or every 2, 3, 4, 5, 6, 7 days.

The duration of the treatment depends on the severity of the disease and ranges from a treatment of some weeks to a chronic treatment.

The tests carried out by the present inventors demonstrated that the siRNAs of the invention are effective in restoring osteoclast functionality in a broad spectrum of dosages, of from about 1 ng/kg of body weight to about 100 mg/kg of body weight of the subject to be treated, or subject in which symptoms of osteopetrosis progression have appeared. In a preferred embodiment, the dosages will be from about 1 μg/Kg to 20 mg/Kg of body weight, preferably from about 1 mg/Kg to about 10 mg/Kg.

To be able to assay the in vivo efficacy of the siRNAs as potential medicaments, the following methodology was adopted:
1. It was verified that the siRNA for clcn7 normal mRNA were effective in reducing normal gene expression in WT mice.
2. It was verified that the siRNA against clcn7 mutated mRNA were not altering normal gene expression.
3. It was verified that the siRNA against clcn7 mutated mRNA were effective in reducing the mutated mRNA and in ameliorating the phenotype of ADO2 mice.

The procedures for such verifications are described in the experimental examples.

Combined Therapy

The siRNAs of the invention can be used in association with other active principles. By the term "in association" it is meant both a co-therapy or combined therapy, and a co-formulation in a single pharmaceutical form, or in a single commercial package, e.g. a kit or a blister of two or more active principles.

Active principles combinable with the siRNAs are for instance agents able to increase bone tissue anabolism: e.g. teriparatide, blosozumab, romosozumab, or even bone growth factors or nucleic acids encoding them, e.g., proteins of the BMP family, such as BMP-2 and/or BMP-7, or RNAs, like e.g. RNAs antagonizing the MIR-31, or transfection agents such as, e.g., lipofectamine, nucleofection by Amaxa Nucleofector® method (Lonza, Cologne, Germany) using a specific kit (Cat# VPA-1007, Lonza).

EXPERIMENTAL SECTION

Example 1: Generation of Vectors Carrying the Constructs of CLCN7 Gene Conjugated with the Sequence for EGFP (Enhanced Green Fluorescent Protein)

Figure 1:
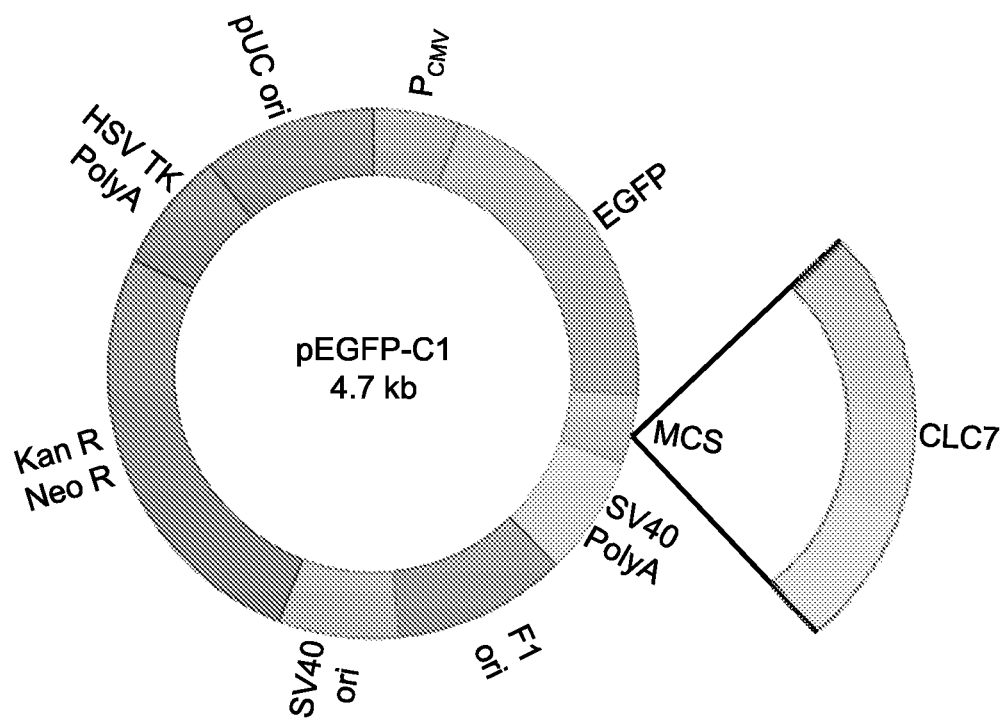
FIG. 1—Scheme of WT-CLCN7 construct, obtained by cloning of the complete sequence of human CLCN7 cDNA in the pEGFP-C1 expression vector, by restriction enzymes HindIII and XhoI.

To be able to perform the experiments in vitro, expression vectors were generated carrying the WT construct of the CLCN7 gene, conjugated with the EGFP sequence to allow visualization of the fusion protein by fluorescence analysis and quantification of the transcriptional expression of the gene by real-time RT-PCR for EGFP (WT CLCN7/pEGFP-C1) (FIG. 1). For that purpose, the full sequence of human CLCN7 cDNA (http://www.ncbi.nlm.nih.gov/nuccore/NM_001114331.2) (rzpd IRAUp969B0859D6) was cloned in the pEGFP-C1 vector by restriction enzymes HindIII and XhoI. The full human sequence of the CLCN7 gene was amplified by iProof™ High-Fidelity DNA Polymerase kit (BIO-RAD 172-5301) using primers with the 5' end provided with the sequences of restriction enzymes HindIII and XhoI. Then, a double digestion of the empty pEGFP-C1 vector and of the PCR product of CLCN7 was performed for 3 hours at 37° C., using the restriction enzymes HindIII and XhoI. The digested vector and PCR product were purified by QIAquick PCR Purification Kit (Qiagen 28104). Then, dephosphorylation of the digested vector was performed, for 1 hour at 37° C., using Shrimp Alkaline Phosphatase (SAP). 300 ng of the digested CLCN7 PCR product and 100 ng of the dephosphorylated pEGFP-C1 vector were ligated by T4 DNA ligase, overnight at 4° C. Ligation was then used to transform XIBlue1 cells. Subsequently, vectors with mutated construct p.R767W-, p.G215R, -p.A788D- and p.R286W-CLCN7/pEGFP-C1 were obtained by QuikChange II XL Site-Directed Mutagenesis Kit (Cat.#6200521, Stratagene), using primers containing the desired mutation. Occurred mutagenesis was then checked by direct DNA sequencing (FIG. 2).

Example 2: Transfections

Figure 3:
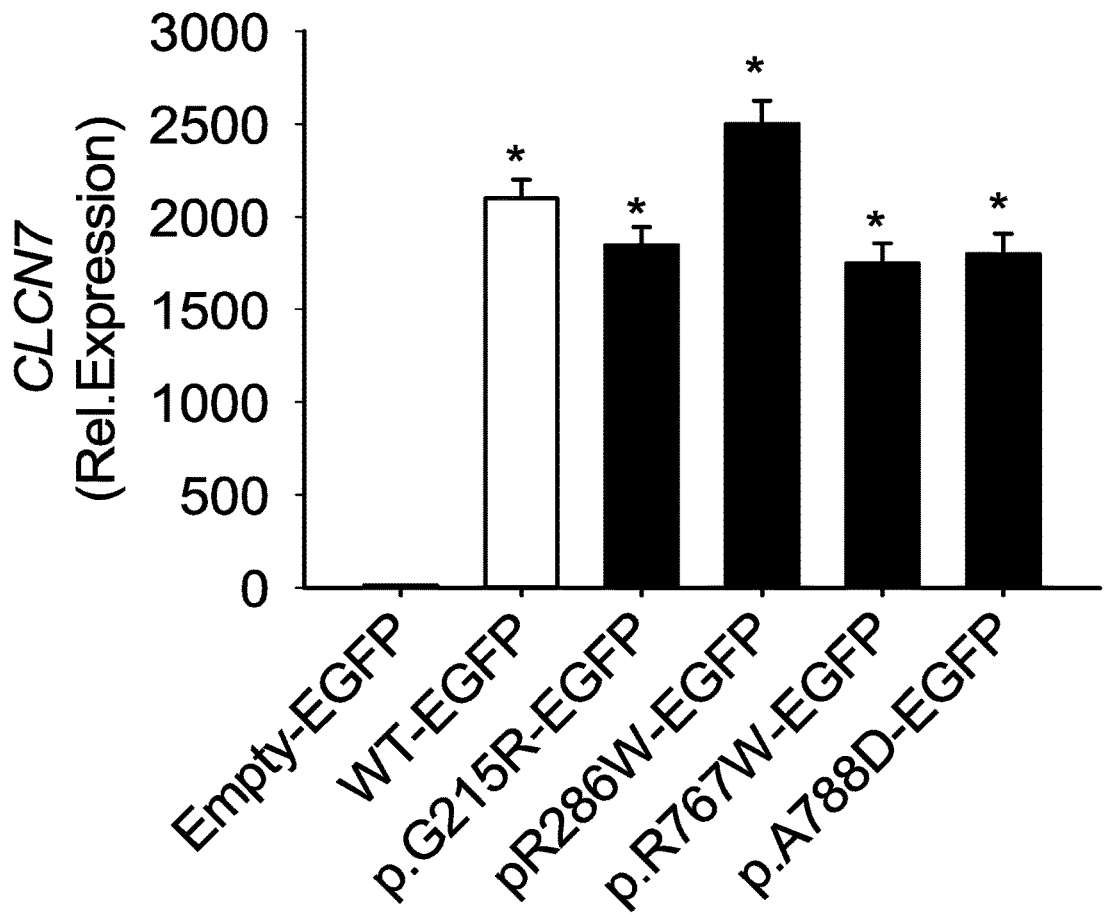
FIG. 3—HEK293 cells were transfected with empty vector or with WT-, p.R767W-, p.G215R-, p.R286W- and p.A788D-EGFP vector. CLCN7 relative expression was quantified by real-time RT-PCR. Mean±s.e. normalized for GAPDH *$p<0.000001$ vs. cells transfected with empty EGFP plasmid (Student's t test).

The vectors were used to transfect human HEK293 cells by standard transfection technique with lipofectamine, then expression of the corresponding mRNA was quantified by real-time RT-PCR. Transfections of the WT construct and of the mutated constructs induced similar levels of transcriptional expression (FIG. 3).

Figure 4:
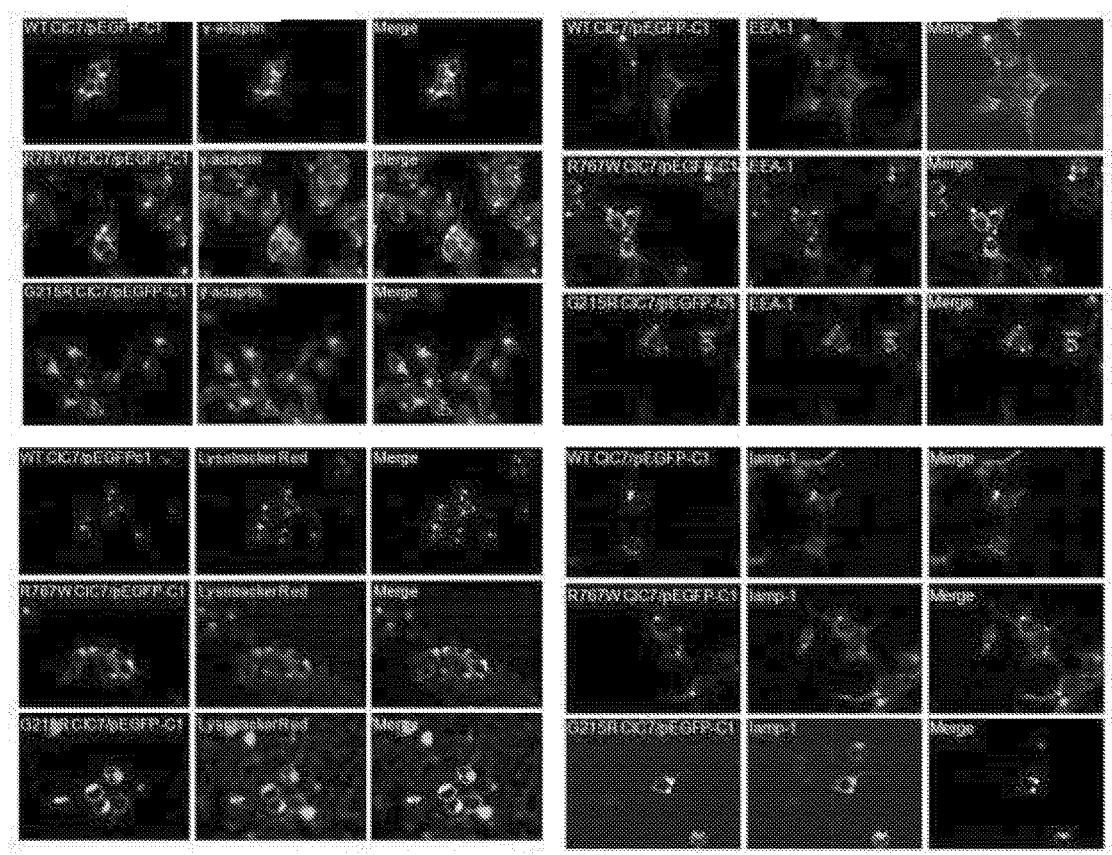
FIG. 4—HEK293 cells were transfected with vectors carrying WT-EGFP, p.R767W-EGFP and p.G215R-EGFP constructs, then the expression and the localization of the fluorescent fusion protein EGFP was detected by confocal microscopy along with the expression of Golgi apparatus markers (gamma-adaptin), early endosomes (EEA1), acid vesicles (Lysotracker Red) and lysosomes (lamp-1). Co-localization of the fusion protein EGFP with the indicated markers is shown in the "merge" panels. Objective lens magnification=63X. Similar results were obtained also for mutations p.A788D and p.R286W (not shown).

Then, expression of WT- and mutated proteins in transfected HEK293 cells was assessed by confocal microscopy for the detection of fusion proteins EGFP. Correct localization of the fluorescent protein was demonstrated by co-localization of Golgi apparatus markers (gamma-adaptin), early endosomes (EEA-1), acid vesicles (Lysotracker Red) and lysosomes (lamp-1) (FIG. 4).

Figure 5:
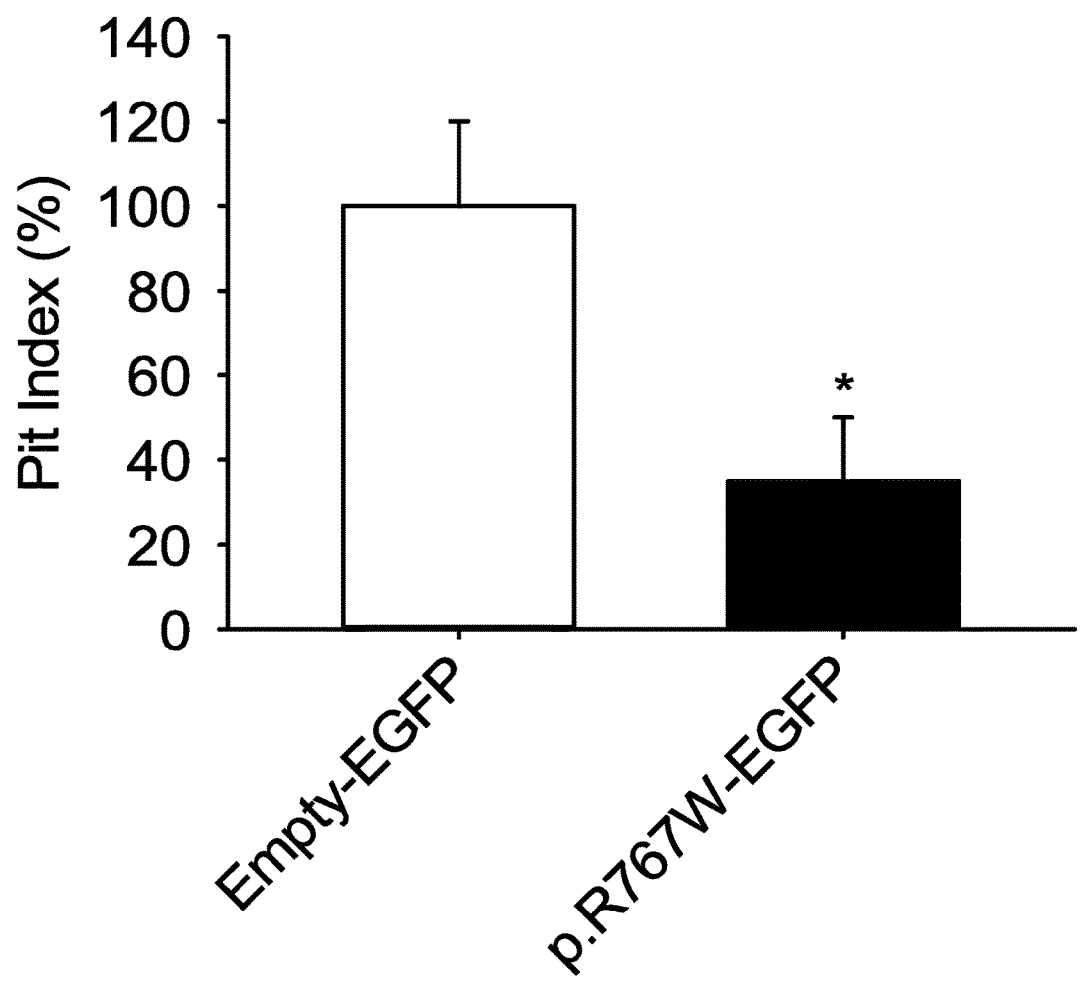
FIG. 5—RAW264.7 cells were transfected with empty EGFP vector or with p.R767W-EGFP vector and differentiated into osteoclasts on bovine bone slices, by treatment with 100 ng/ml RANKL. The slices were then sonicated to remove cells and assessed for resorption lacuna (pit) formation (pit index) after staining with 0.1% toluidine blue. Mean±s.e. *$p<0.05$ vs. cells transfected with empty EGFP vector (Student's t test).

To demonstrate the ability of the mutated constructs of the Inventors to be expressed in the osteoclast line and inhibit bone resorption, the murine line of RAW264.7 osteoclast precursors was transfected with empty vector, or with a vector carrying the mutated constructs. mRNA and protein expressions were checked by real-time RT-PCR and confocal microscopy, respectively, then the cells were plated onto bovine bone slices and differentiated into mature osteoclasts by treatment with 100 ng/ml RANKL for 4 days. Bone resorption was quantified by count of the resorption lacunae (pits) dug out by osteoclasts (pit index assay). The results demonstrated a bone resorption reduction of about 70% in RAW264.7 cells transfected with the mutated constructs, compared to the same cells transfected with the empty vector (FIG. 5). This percentage of bone resorption is very similar to that observed in osteoclasts differentiated from the peripheral blood of ADO2 patients, compared to osteoclasts from healthy donors (6).

Figure 6:
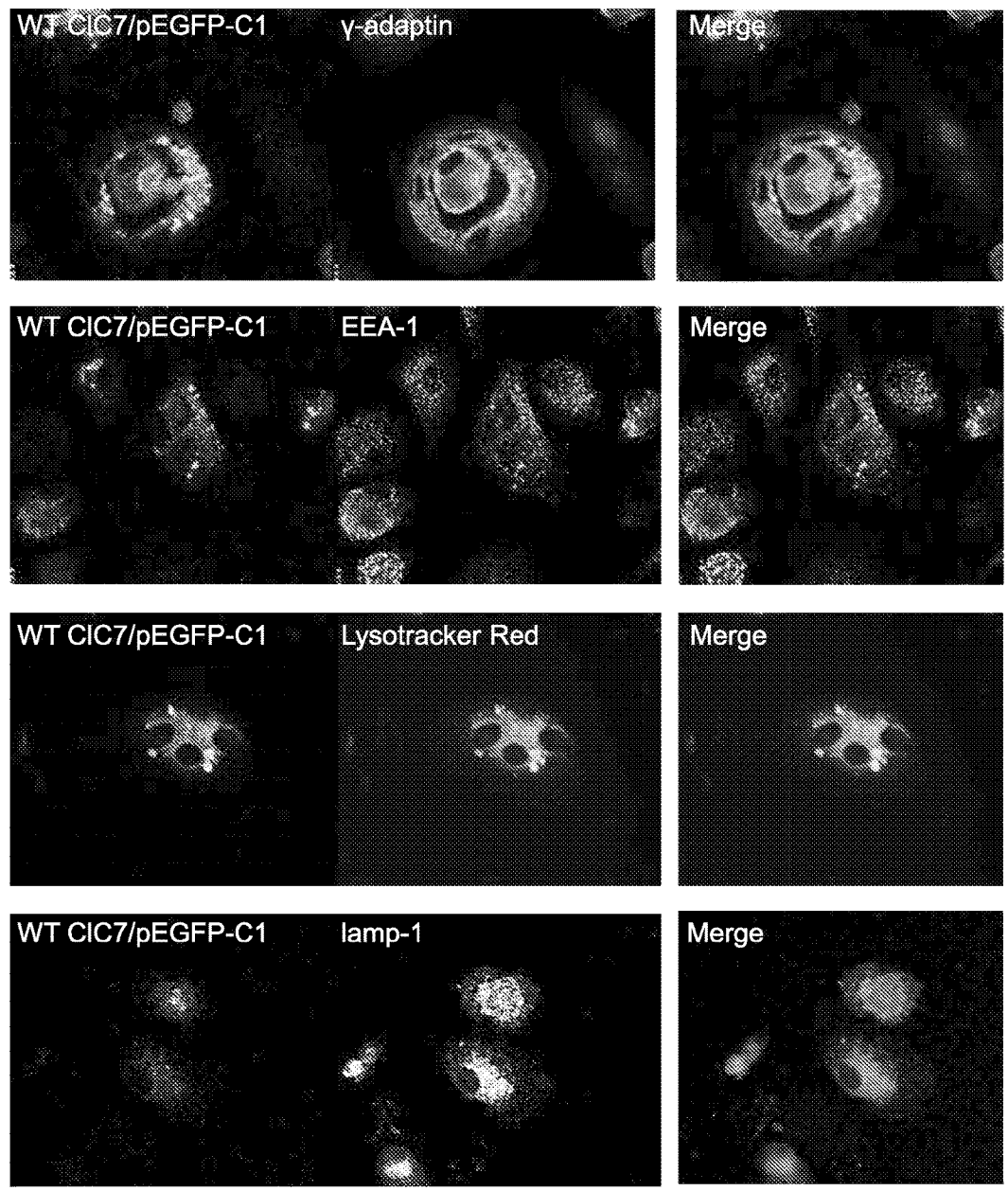
FIG. 6—Human osteoclasts were differentiated from peripheral blood mononuclear cells of a healthy donor, by incubation for 14 days with 20 ng/ml M-CSF and 30 ng/ml RANKL. Cells were transfected with WT-EGFP vector by the AMAXA method. After 2 days, the fluorescence of the EGFP fusion protein was detected by confocal microscopy. The correct co-localization with the markers indicated for the Golgi apparatus (gamma-adaptin), early endosomes (EEA-1), acid vesicles (Lysotracker Red) and lysosomes (lamp-1) is shown in the "merge" panels. Objective lens magnification=63X.

These experiments yielded good evidence that the generated vectors might represent valid tools for evaluating the Inventors' strategy of in vitro silencing of the mutated gene. However, to verify that the method would work also in primary human osteoclasts, a nucleofection process by AMAXA nucleofector was set up. The procedure was successful, enabling a good hyperexpression of the Inventor's EGFP fusion protein in osteoclasts differentiated from peripheral blood mononuclear cells of healthy donors (FIG. 6).

Assessment of bone resorption in human osteoclasts transfected with the human constructs demonstrated once more a 70% reduction compared to cells transfected with the empty vector (not shown).

Example 3: In Vitro Treatments with siRNA

After having set up the investigation methods, siRNAs against the abovementioned mutations of the CLCN7 gene (Table 2) were designed and assigned for synthesis to Dharmacon Company. Moreover, the commercial pool of siRNA against WT CLCN7 gene and scrambled (mixed nucleotide sequence) control siRNA was purchased.

Figure 7:
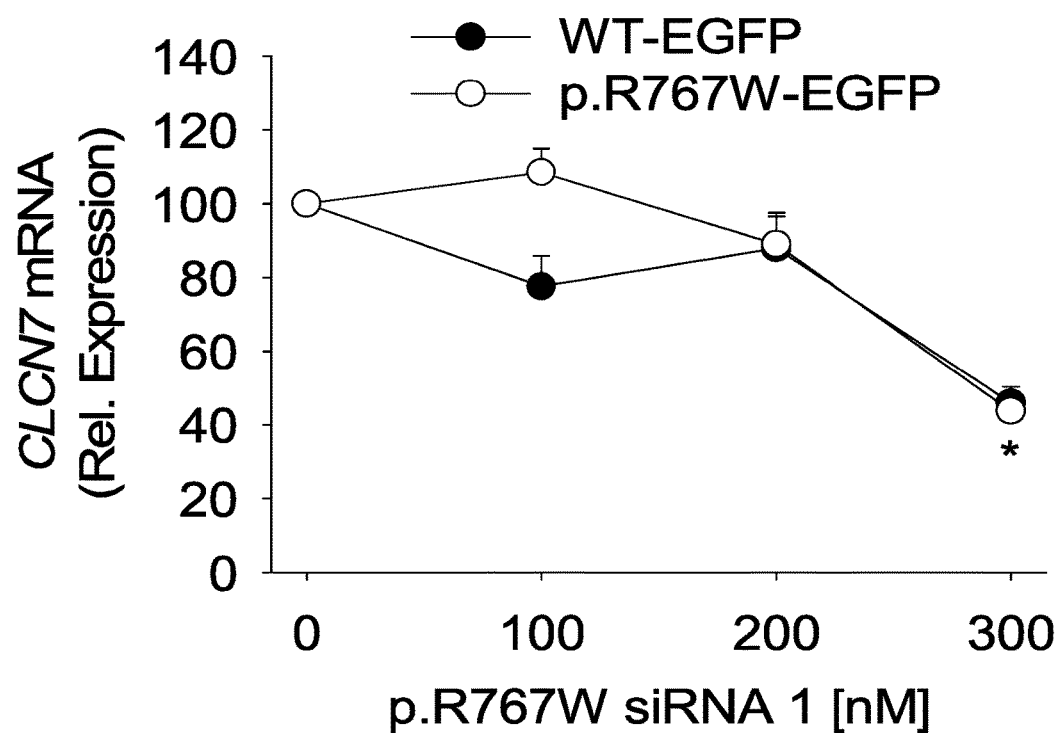
FIG. 7—HEK293 cells transfected with WT vectors or carrying the mutation p.R767W of the CLCN7 gene and treated with control scrambled siRNA or with increasing concentrations of p.R767W 1 siRNA for 48 hours. At the end of the incubation, the RNA was extracted and the expression of the CLCN7 transcript was assessed by real-time RT-PCR. Mean±s.e. normalized for GAPDH, expressed as percentage over the treatment with scrambled siRNA (point 0 on the X-axis). *$p<0.05$ vs. cells transfected with p.R767W- and WT-EGFP treated with control (SCR, scrambled) siRNA (Student's t test).

The setting up of the procedure was performed with siRNA against p.R767W mutation. It was then extended to the other mutations. A siRNA specific for the trascriptor carrying the p.R767W mutation (R286W siRNA 1) was assessed for efficacy and specificity in HEK293 cells transfected with WT- or p.R767W-ClCN7/EGFP vectors. The results showed a ≤60% reduction of mutated mRNA expression. However, this positive result was invalidated by a similar reduction of normal mRNA in cells transfected with the WT CLCN7/EGFP vector (FIG. 7).

Figure 8:
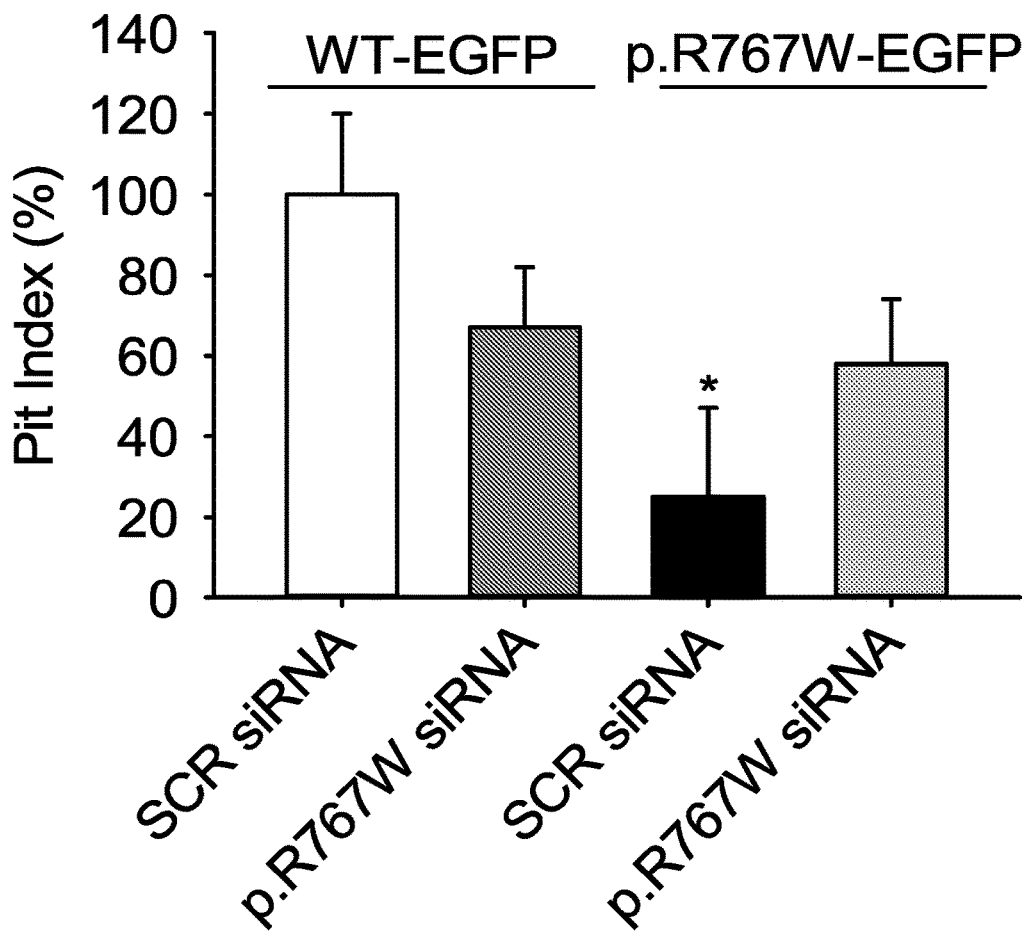
FIG. 8—RAW264.7 cells were transfected with empty vector or with WT- or p.R767W-EGFP vectors, differentiated into osteoclasts on bovine bone slices and treated with control (SCR) siRNA, or with siRNA specific for the transcript bearing the mutation p.R767W (p.R767W 1 RNA). Quantification of bone resorption shows the ability of p.R767W 1 siRNA to improve bone resorption reduced by the mutated construct (compare black and light grey bars). Instead, p.R767W 1 siRNA did not significantly modify bone resorption in cells transfected with WT-EGFP vector (compare white and dark grey bars). Mean±s.e. *$p<0.05$ vs. cells transfected with empty EGFP vector (Student's t test).

Although this siRNA showed no specificity for the mutated gene, its good efficacy in reducing the mRNA of the mutated transcript was encouraging. Therefore, its effect on bone resorption was assessed by using RAW264.7 cells transfected with the R767W- or WT-CLCN7/EGFP construct. Under these experimental conditions, it was demonstrated that the siRNA for the mutated mRNA showed a partial ability to reactivate bone resorption compared to control scrambled siRNA. In this experiment, a modest inhibition of bone resorption was observed in cells transfected with WT-CLCN7/EGFP vector and subjected to treatment with siRNA against p.R767W mutation (FIG. 8). This reduction, lower than what observed in cells transfected with mutated vector (compare second and third bar from the left) might be due to abundance of CLCN7 mRNA expression in RAW264.7 cells, due to the presence both of endogenous mRNA and of mRNA produced by the transfected construct.

At this point, a strategy for increasing the specificity toward the mutated mRNA was adopted. This was obtained by inserting a non-complementary (mismatch) nucleotide in various positions downstream of the mutated nucleotide (11). With this strategy, three novel siRNA for p.R767W mutation were designed (Table 2). All three siRNAs showed greater specificity for the mutated mRNA compared to the WT mRNA. With one of them (termed p.R767W siRNA 2C), a 90% efficacy of mutated mRNA reduction was obtained, without any reduction of WT mRNA (FIG. 9).

Then, human osteoclasts were treated with siRNA for the normal CLCN7 gene using siRNAs conjugated with Cy3 fluorophore (Cy3-WT siRNA). The aim was to set up the strategy of siRNA internalization into primary cells, using confocal microscopy for its checking. Under these conditions, it was observed that osteoclasts internalize the siRNAs with no need of any transfection agent. In fact, incubation, under standard culture conditions, of osteoclasts differentiated from peripheral blood mononuclear cells of healthy donors with 300 nM Cy3-WT siRNA highlighted siRNA incorporation into the cell and its preservation up to +7 days from treatment (FIG. 10A).

To demonstrate the ability of R767W siRNA C to reduce CLCN7 mutated p.R767W expression and decrease its detrimental effect on bone resorption, human osteoclasts were transfected with the p.R767W CLCN7/pEGFP vector and treated with 500 nM p.R767W siRNA 2C. Under these circumstances, there were highlighted a reduced transcriptional expression of the EGFP fluorescent protein sequence (FIG. 10B) and the restoration of osteoclasts' ability to resorb bone (FIG. 10O) in cells treated with p.R767W siRNA 2C, compared to osteoclasts treated with scrambled siRNA.

Figure 11:
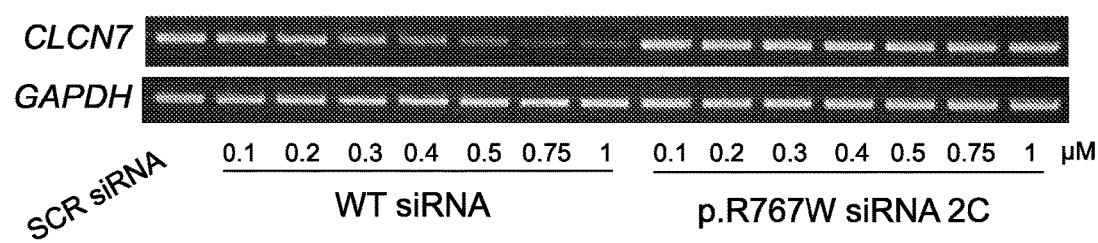
FIG. 11—Human osteoclasts were differentiated from peripheral blood mononuclear cells of a healthy donor and treated for 48 hours with the concentrations of WT siRNA or p.R767W siRNA 2C indicated in the figure. RNA was extracted and subjected to RT-PCR. Note the absence of effect of p.R767W siRNA 2C on expression of normal CLCN7 transcript (normalized for GAPDH).
Figure 12:
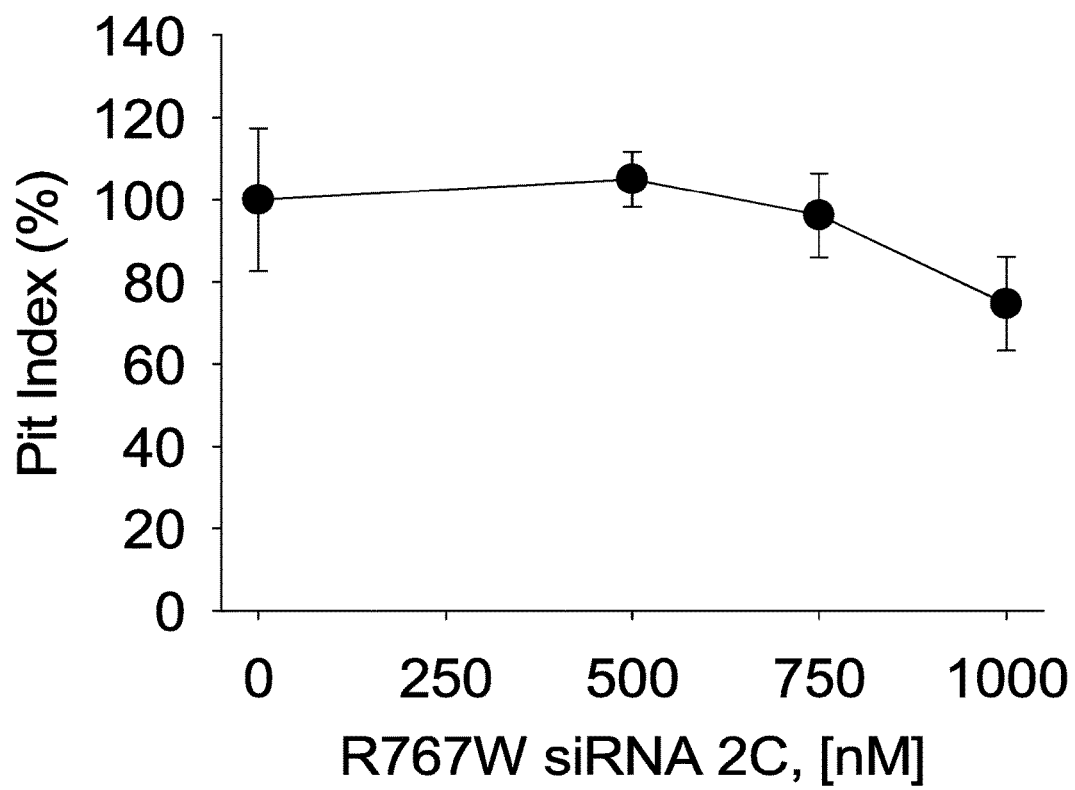
FIG. 12—Human osteoclasts were differentiated from peripheral blood mononuclear cells of a healthy donor, plated on bone slices, incubated and treated for 48 hours with scrambled siRNA or with the indicated concentrations of p.R767W siRNA 2C. Bone resorption was then quantified by pit assay. Mean±s.e. expressed as percentage over the treatment with scrambled siRNA (point 0 on the X-axis). Note the absence of a statistically significant effect in resorption pit formation by the treatment with p.R767W siRNA 2C (Student's t test).

Then, it was evaluated whether the treatment with p.R767W siRNA 2C influenced the transcriptional expression of the normal CLCN7 transcript and the ability to resorb bone in human osteoclasts from a healthy donor. The results showed a good effectiveness of the siRNA directed against normal CLCN7 (used as positive control) in decreasing this mRNA, whereas no effect thereon by p.R767W siRNA 2C was observed (FIG. 11). In accordance with this result, p.R767W siRNA 2C did not modify the bone resorption of osteoclasts from healthy donors (FIG. 12).

Overall, these results show that the strategy of the Inventors was successful and allowed them to design highly specific siRNAs against the p.R767W mutation of the CLCN7 gene, which had no effect on the normal mRNA of human osteoclasts.

Figure 13:
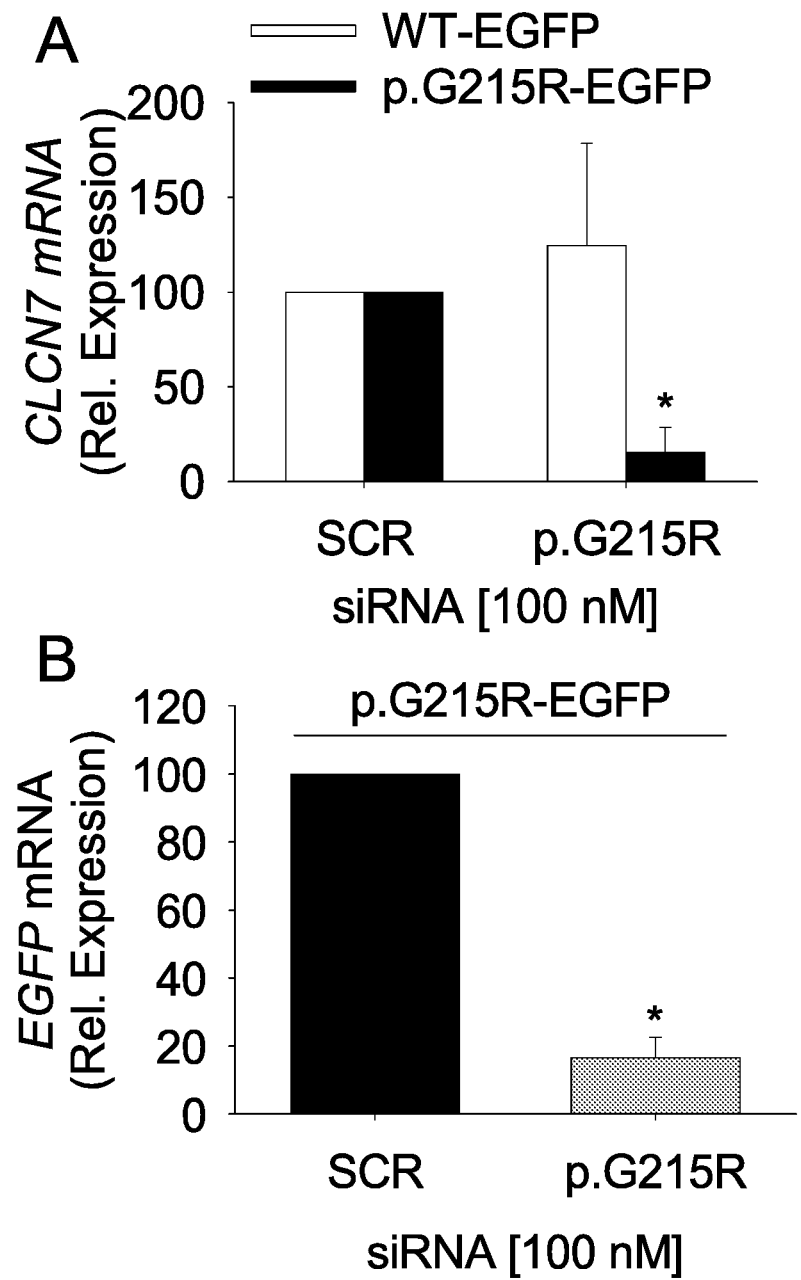
FIG. 13—(A) HEK293 cells and (B) primary human osteoclasts were transfected with WT- or p.G215R-EGFP vectors and treated for 48 hours with 100 nM of control (SCR, scrambled) siRNA, or of p.G215R-EGFP (p.G215R)-specific siRNA. CLCN7 mRNA expression was assessed by real-time RT-PCR, using primers specific for CLCN7, for HEK239 cells (which do not express the endogenous gene CLCN7), and for EGFP for human osteoclasts (to distinguish the mutated exogenous CLCN7 gene from the normal endogenous one). Mean±s.e. normalized with GAPDH (Student's t test).
Figure 28:
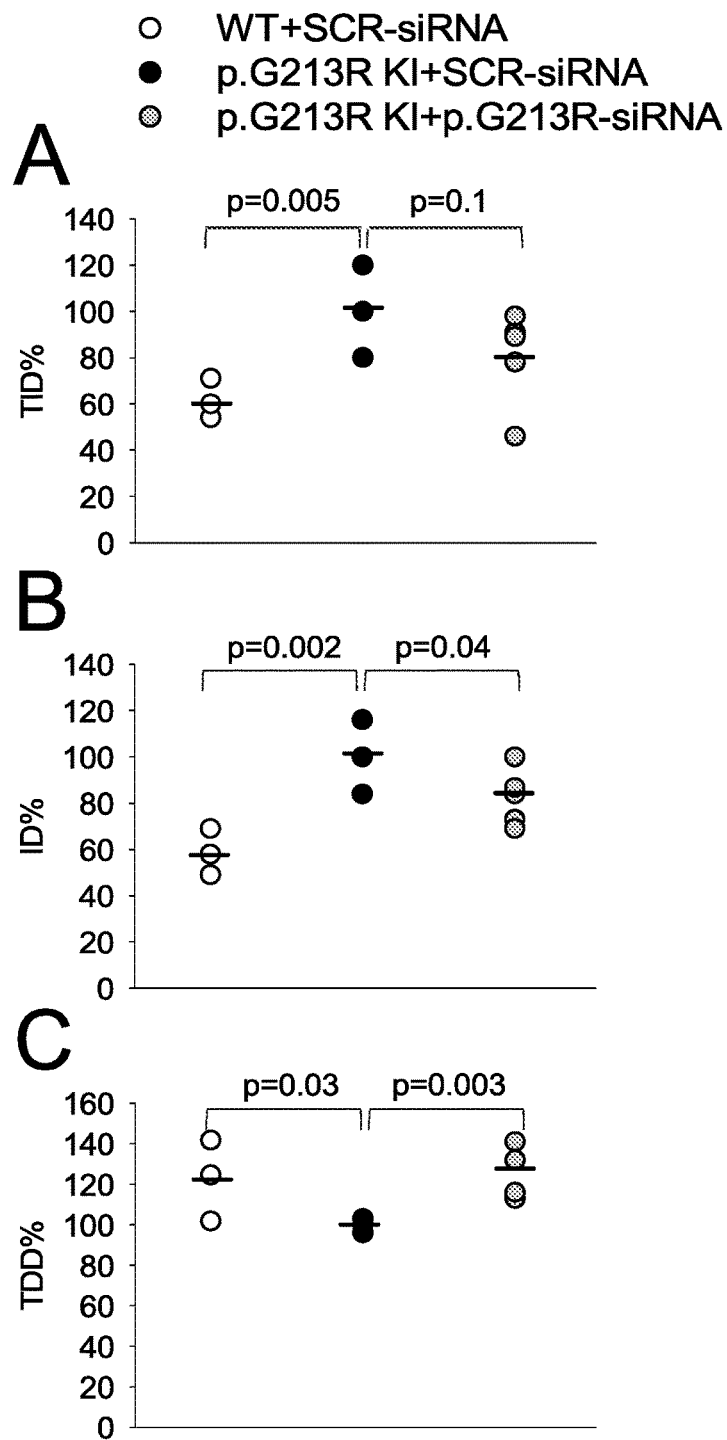
FIG. 28—Analysis of bone quality by indentation in mice described in FIG. 25. (A) Total indentation distance (TID).

Following the same strategy, siRNAs against the other aforedescribed three mutations, p.G215R, p.A788D and p.R286W (Table 2) were designed. From a detailed analysis of the results, it emerged that for the p.A788D mutation siRNAs meeting the efficacy and specificity criteria required for their use in the therapy of CLCN7-dependent ADO2 have not been identified yet. As to mutations p.R286W and p.G215R, siRNAs were instead identified for which the efficacy and specificity criteria were met (Table 2). Since for the p.G215R siRNA mutation a murine model of disease is presently available, the features of the effective siRNA identified in Table 2 with the abbreviation p.G215R 2M were studied. It proved highly active in reducing the expression of mutated mRNA in HEK293 cells and in primary human osteoclasts (FIG. 13, FIG. 28).

Figure 14:
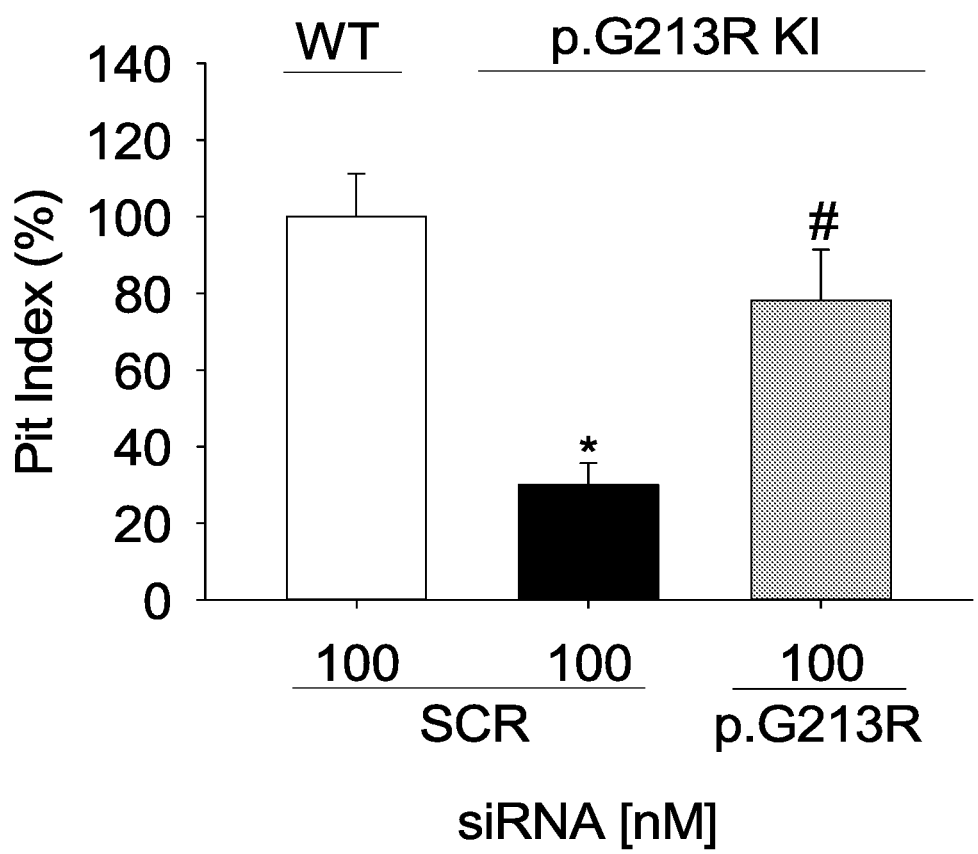
FIG. 14—Primary osteoclasts, generated from the bone marrow mononuclear cells of WT- and p.G213R-clcn7 ADO2 (p.G213R KI) mice by incubation with 50 ng/ml M-CSF and 120 ng/ml RANKL, were plated on bone slices and treated for 7 days with control (SCR) siRNA, or p.G213R-clcn7 (p.G213R) specific siRNA, at the concentration of 100 nM. At the end of the incubation, cells were removed by sonication, slices were stained with 0.1% toluidine blue and bone resorption was evaluated by pit assay. Mean±s.e. *p=0.0001 vs. WT, #p=0.003 vs. p.G213R KI (Student's t test).

Moreover, by using murine osteoclasts from the animal ADO2 model generated in the laboratory of the Inventors (10), carrying the murine homologue (p.G213R) of the human mutation (p.G215R), it was demonstrated that the treatment with p.G213R siRNA (Table 3) was able to increase bone resorption (FIG. 14).

Example 4: In Vivo Treatments

To be able to assay siRNAs efficacy in vivo, as medicaments, the following procedure was followed:
i) Verifying that the siRNA for clcn7 normal mRNA be effective in reducing normal gene expression in WT mice.
ii) Verifying that the siRNA against clcn7 mutated mRNA does not alter normal gene expression.
iii) Verifying that the siRNA against clcn7 mutated mRNA be effective in reducing the mutated mRNA and in ameliorating ADO2 mice phenotype.

i) Verifying that the siRNA for Clcn7 Normal mRNA be Effective in Reducing Normal Gene Expression in WT Mice.

Figure 15:
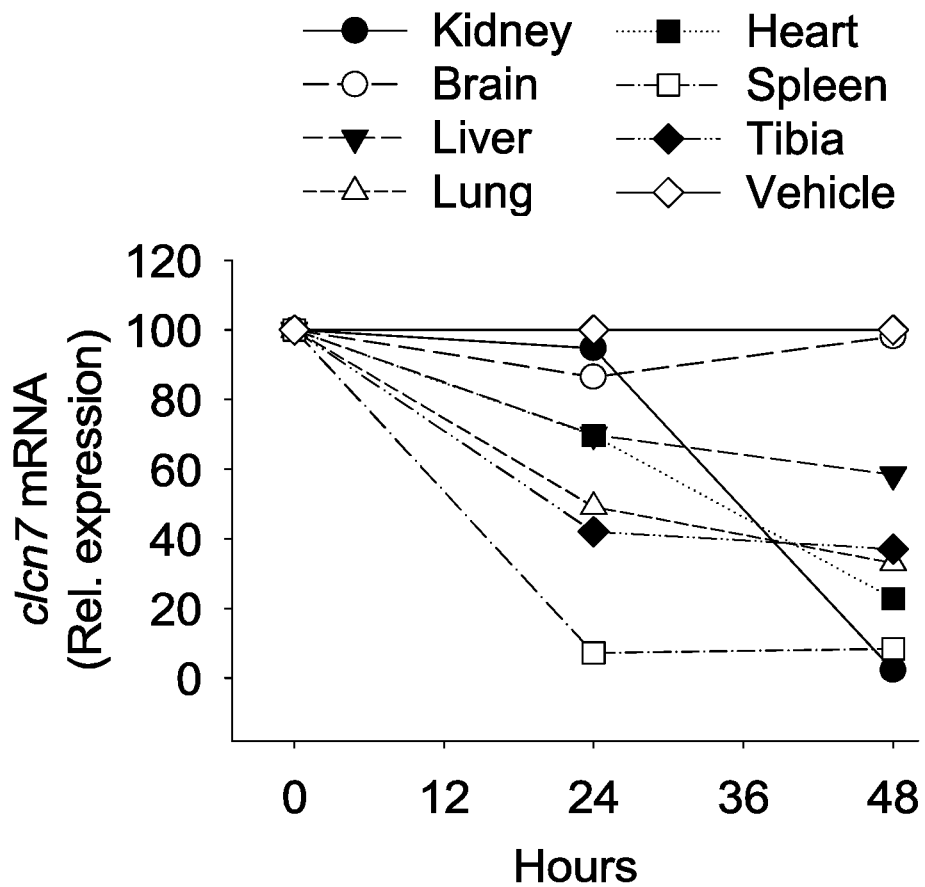

This group of experiments was carried out with a pool of siRNAs against the normal clcn7 gene, available on the market by Dharmacon, whose nucleotide sequence is unknown. 1-month old CD1 mice (n=4) were treated with 2 mg/Kg clcn7-siRNA inoculated by TransIT-QR (Quick Recovery) Hydrodynamic Delivery kit. The TransIT solution is specifically studied for safe and effective administration of nucleic acids, using the hydrodynamic injection procedure in the tail vein. After 24-48 hours, animals were sacrificed and subjected to anatomical dissection to collect heart, spleen, liver, kidneys, brain, lungs and tibias (FIG. 15). This latter result probably depends on clcn7-siRNA inability to cross the blood-brain barrier.

Then, in normal CD1 mice it was also ascertained which were the best clcn7-siRNA administration pathway, in order to verify the feasibility of repeated treatments. Injection by TransIT-QR Hydrodynamic Delivery kit proved effective, but it can be performed only once and on adult mice. Intraperitoneal administration proved easy to perform from the animals' first days of life. Venous infusion was also efficient, but it was possible to perform it only on adult mice and for a very limited number of times. Therefore, intraperitoneal injection was chosen for subsequent studies. Moreover, the best administration frequency was tested to be of 48 hours, by which the best dose-dependent response was demonstrated both in bone and in other organs. The maximum dose used in this series of experiments (0.5 mg/Kg of body weight), administered 3 times a week for 3 weeks, induced no modifications of structural bone parameters, measured by computerized microtomography (µCT). The Inventors explain this negative result with the notion that the gene is haplosufficient and that this treatment regimen has reduced the clcn7 mRNA only of 60%, leaving a 40% of mRNA probably sufficient for the carrying out of its functions. In any case, the treatment induced no sign of suffering, nor did it cause any evident distress to the animals.

ii) Verifying that the siRNA Against Clcn7 Mutated mRNA does not Alter Normal Gene Expression and does not Induce Adverse Effects.

To demonstrate this aspect, normal CD1 mice were treated with p.G213R-clcn7 siRNA (Table 3) (0.5 mg/Kg) and it was observed that there was no reduction of the normal transcript, unlike what found in the treatment with the clcn7-siRNA directed against the normal transcript. In all these experiments, the control scrambled siRNA never caused alterations of the expression of the clcn7 gene, neither normal, nor mutated. With these experiments the Inventors therefore demonstrated that the siRNAs for one of the mutations of the clcn7 gene are ineffective towards the normal transcript and do not induce adverse side effects.

iii) Verifying that the siRNA Against Clcn7 Mutated mRNA be Effective in Reducing the Mutated mRNA and in Improving ADO2 Mice Phenotype To test the effectiveness of their treatment, an experiment was therefore carried out in the sole murine ADO2 model available (12). This model was created in C57BL/6 mice strain by knock-in technology, which allowed substitution of the normal hexon 7 of the clcn7 gene with a hexon 7 mutated by a G-A transition in position 14365 of the DNA, corresponding to the protein mutation p.G213R.

Mice homozygous for this mutation are small, lack teeth eruption and die within 30 days from birth, even when fed a soft diet. They exhibit an extremely severe osteopetrotic phenotype, fibrous bone marrow and hippocampal and cerebellar cortex degeneration similar to what found in a clcn7 knock-out murine model and in human autosomal recessive osteopetrosis.

Heterozygous mice are born at the normal Mendelian frequency, are vital and fertile and unaffected by alterations of size, body weight and teeth eruption. They instead exhibit the typical signs of a less severe osteopetrosis, without evident signs of neurodegeneration. Heterozygous adult (3 month-old) mice exhibit greater mineral density and greater bone mass, verified by µCT analysis of trabecular structural bone parameter of the tibias, femurs and vertebrae. This increase of bone mass is persistent, can also be found in old mice, and is similar in males and in females. Histological examination of heterozygous 3 month-old mice showed an increase of the expression of the osteoclast-specific enzyme TRAcP and an increase of osteoclast number/surface/bone surface. Despite this increase, bone resorption is reduced as indicated by serum levels of bone resorption marker CTX normalized for serum activity of osteoclastic enzyme TRAcP. On the contrary, all bone formation parameters [serum marker (osteocalcin), osteoblast surface/bone surface, bone formation rate, osteoid thickness, growth plate thickness] demonstrate that there is no osteoblast or chondrocyte involvement, nor do mice have a phenotype compatible with osteopetrorachitism.

Bone marrow collected from mice shows an increase of the number of osteoclast precursors and a greater osteoclastogenesis in vitro in the presence of M-CSF and RANKL. Nevertheless, bone resorption is reduced compared to osteoclasts obtained from the bone marrow of normal mice. Heterozygous mice have normal hematological and serum parameters (pancreatic amylase, hepatic transaminases, potassium, calcium, phosphorus, muscle creatine kinase and glucose concentration), whereas parathyroid hormone levels are increased, in accordance with increased osteoclastogenesis.

Figure 16:
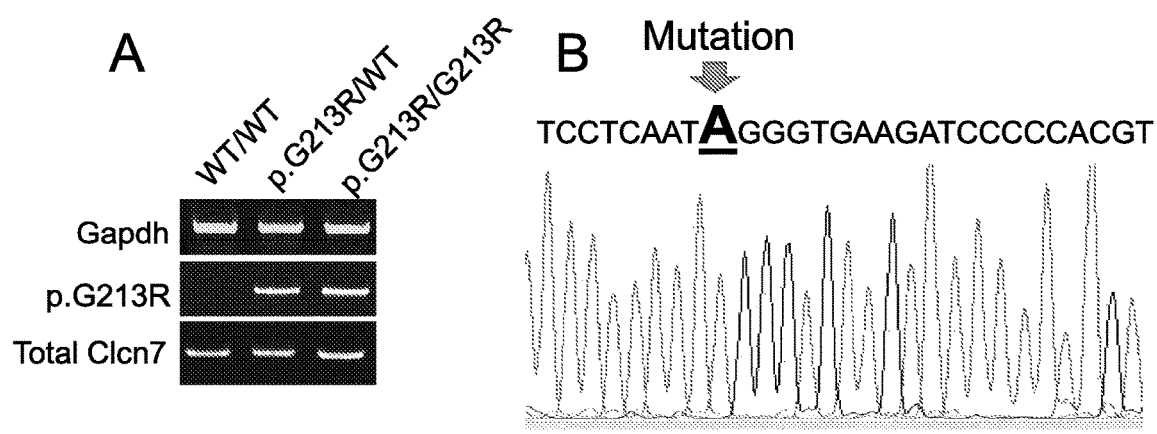
FIG. 16—(A) RT-PCR using primers specific for the p.G213R mRNA (Fw: CAAGTGCTTCCTCAATG (SEQ ID NO:32); Rv: GCCCTCTTCCAAGCTAAA (SEQ ID NO:33) showing transcript amplification only in primary osteoclasts of heterozygous and homozygous p.G213R KI mice, while in wild-type (WT) osteoclasts no transcript appears amplified. (B) Direct DNA sequencing of the amplified transcript shown in figure (A) in heterozygous p.G213R/WT osteoclasts, demonstrating only the mutated sequence.
Figure 17:
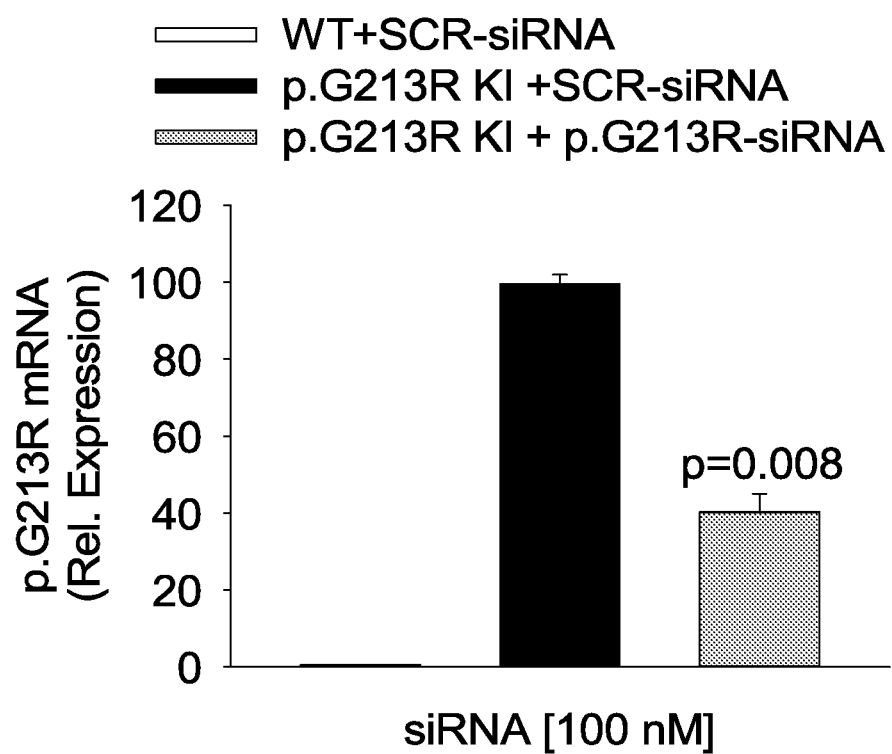
FIG. 17—Osteoclasts generated from bone marrow mononuclear cells of WT and p.G213R KI mice were treated with the indicated concentration of control (SCR) siRNA or p.G213R-clcn7-specific siRNA. Real-time RT-PCR was performed using the primers specific for the mutated transcript indicated in FIG. 14. Mean±s.e. (Student's t test)
Figure 18:
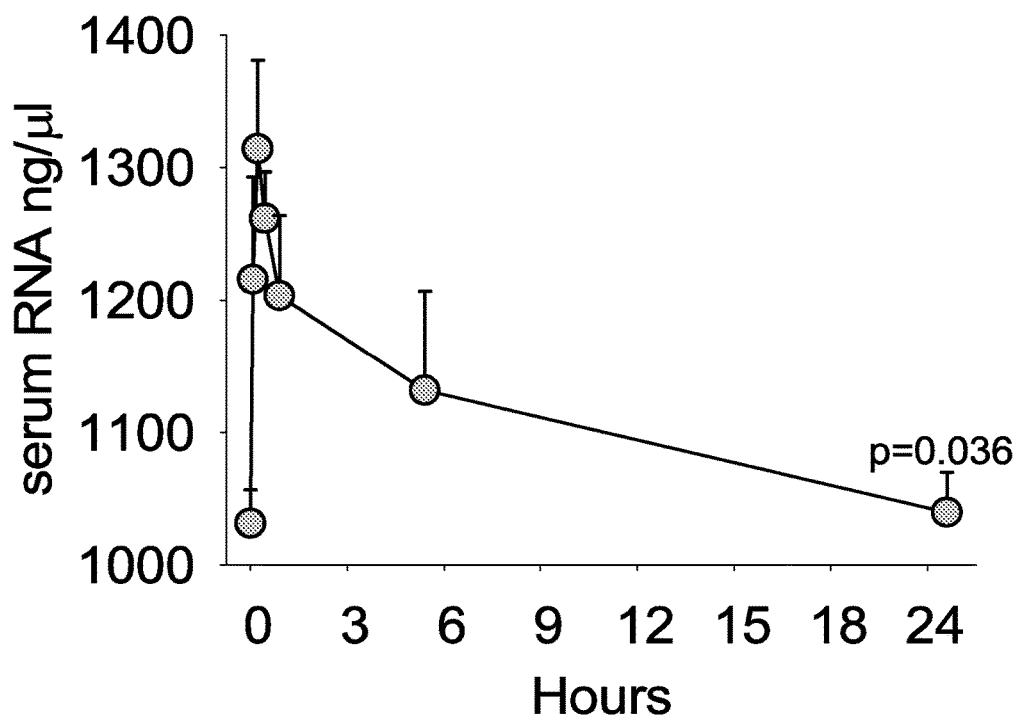
FIG. 18—Three month-old p.G213R KI mice received an intraperitoneal (i.p.) injection of 4 mg/kg of p.G213R-clcn7 sticky siRNA/jetPEI™ (conjugate) and were sacrificed at the indicated time points. Sera were collected and evaluated for total RNA levels by Nanodrop. Mean±s.e. (ANOVA).
Figure 19:
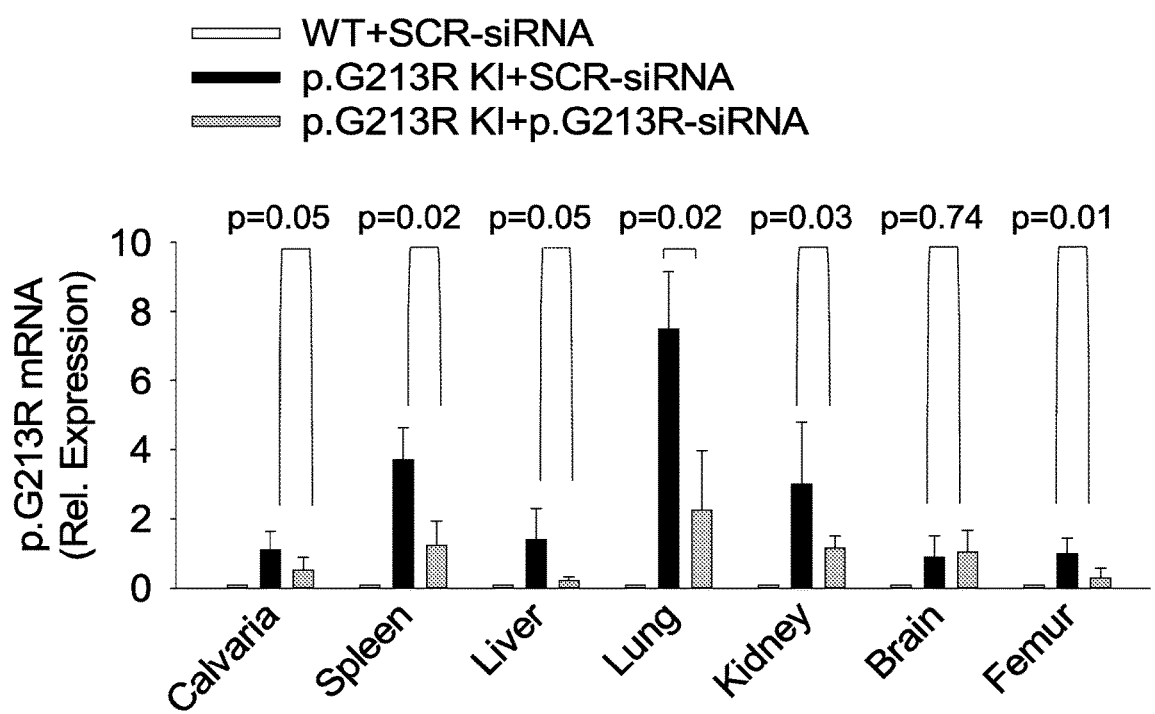
FIG. 19—Ten day-old p.G213R KI mice received an i.p. injection of 4 mg/kg of p.G213R-clcn7 sticky siRNA/jetPEI® conjugate, 3 times a week for 4 weeks. At the end of the experiment mice were sacrificed, RNA was extracted from the organs indicated in figure and subjected to RT-PCR, using primers specific for the mutant transcript indicated in FIG. 14, normalized with gadph. Mean±s.e. (Student's t test)
Figure 20:
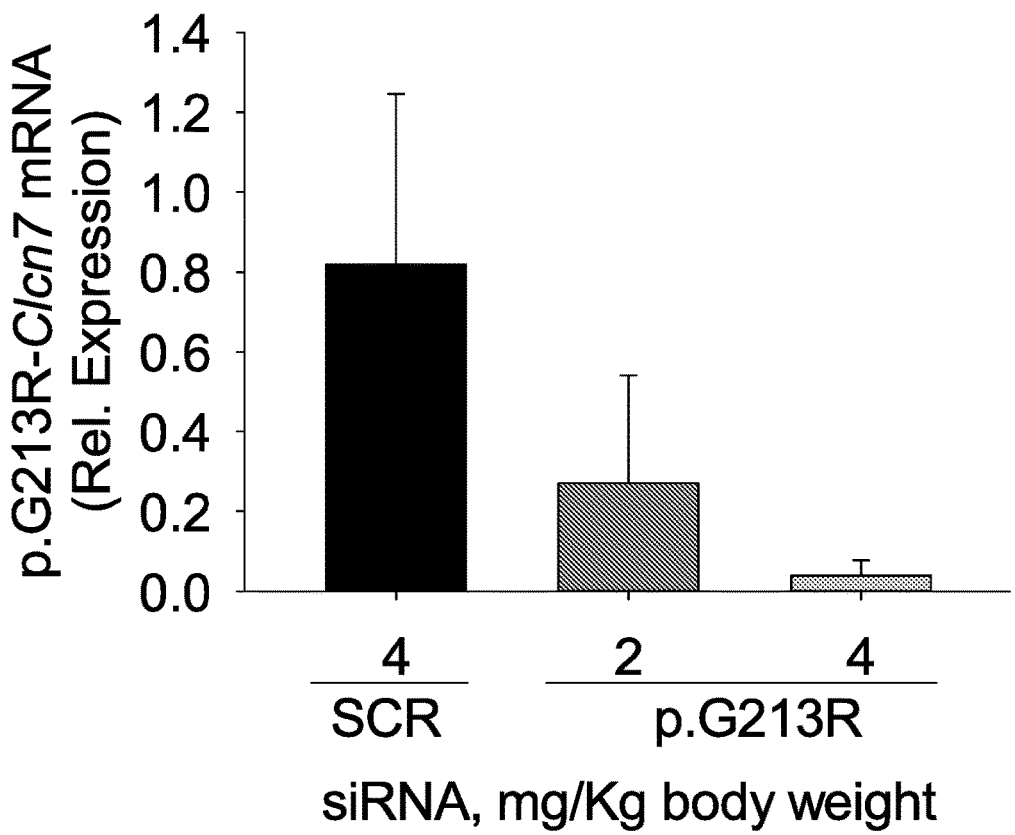
FIG. 20—p.G213R ADO2 mice were subjected to i.p. injection with control (SCR, scrambled) siRNA or p.G213R-clcn7 sticky siRNA/jetPEI (p.G213R), at the doses indicated on the X-axis. After 48 hours, tibias were collected, RNA was extracted and the levels of p.G213R-clcn7 mutated mRNA were evaluated by real-time RT-PCR using the pair of primers specific for the mutated sequence indicated in FIG. 14. Mean±s.e. normalized for GAPDH.

Having obtained a reliable murine ADO2 model, therein it was verified whether the therapy with siRNAs directed against mutation p.G215R were effective. First of all, optimal dose and administration time of p.G213R-clcn7 siRNA were established. To this end, primers able to amplify exclusively the mutated transcript (FIGS. 16 and 17) were first designed. Then, p.G213R-clcn7 ADO2 mice were treated with 2 or 4 mg/Kg of body weight of p.G213R-clcn7 sticky siRNA/jetPEI by intraperitoneal injection, verifying the in-serum kinetics of the total RNA (FIG. 18) and confirming the reduction of p.G213R-clcn7 mutated mRNA expression by real-time RT-PCR in mice treated with p.G213R-clcn7 sticky siRNA/jetPEI compared to mice treated with control (scrambled) siRNA (FIG. 19). This reduction was also confirmed in tibia (FIG. 20) and was not evident anymore after 96 hours from p.G213R-clcn7 sticky siRNA/jetPEI administration, a circumstance indicating the best treatment frequency to be of 48 hours.

Figure 21:
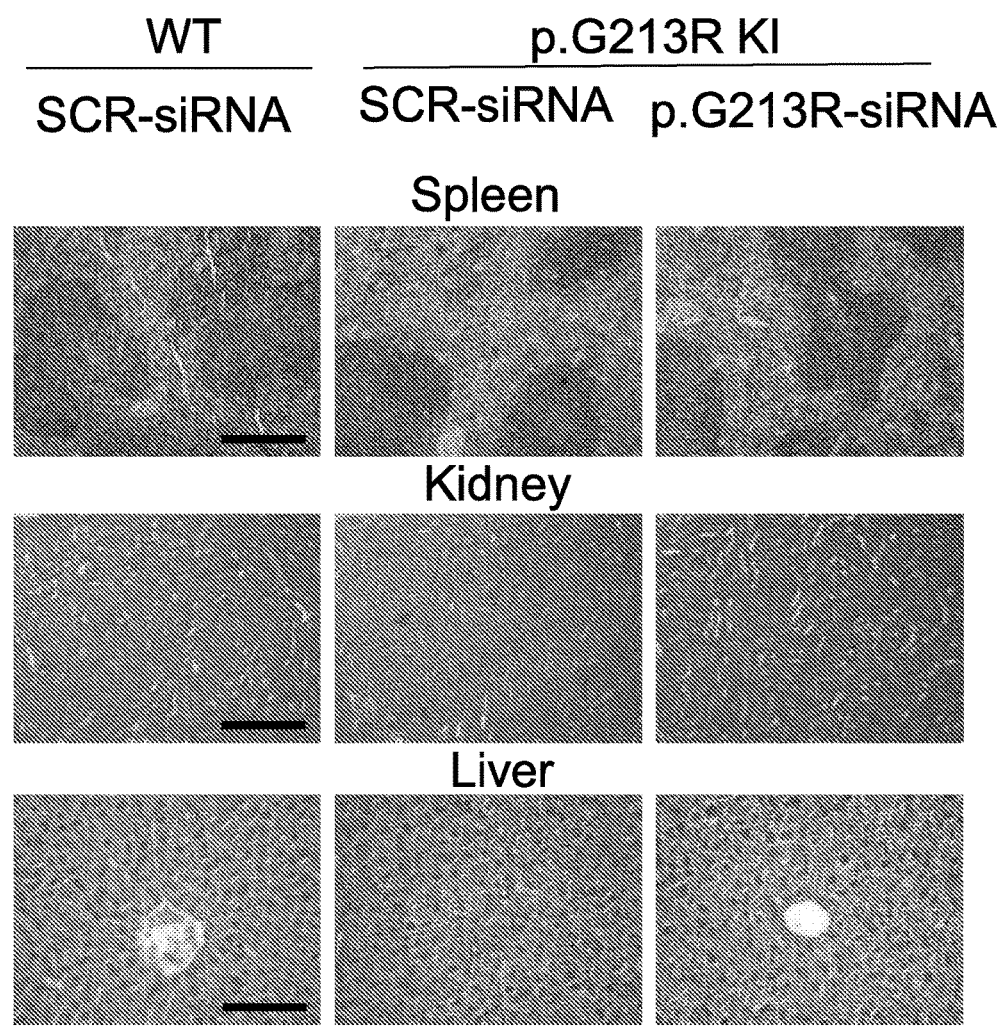
FIG. 21—p.G213R KI mice received i.p. injections of 4 mg/kg of SRC-siRNA or p.G213R-clcn7 sticky siRNA/jetPEI, 3 times a week for 4 weeks. At the end of the experiment, mice were sacrificed and subjected to histopathological evaluation of the organs indicated in Figure by haematoxylin/eosin staining (Bar=100 µm for spleen and kidney, 20 µm for liver).
Figure 22:
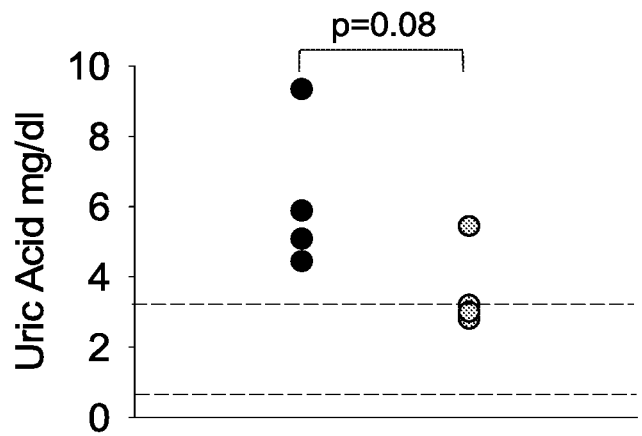
FIG. 22—Sera were collected from the mice described in FIG. 20 and analyzed by Refloton method for the biomarkers of renal (uric acid) and hepatic [glutamic oxaloacetic transaminase (GOT)] functions, and for the ADO2 biomarker creatine kinase (CK). Normal values are comprised between the dotted lines. Mean±s.e. (Student's t test).
Figure 22:
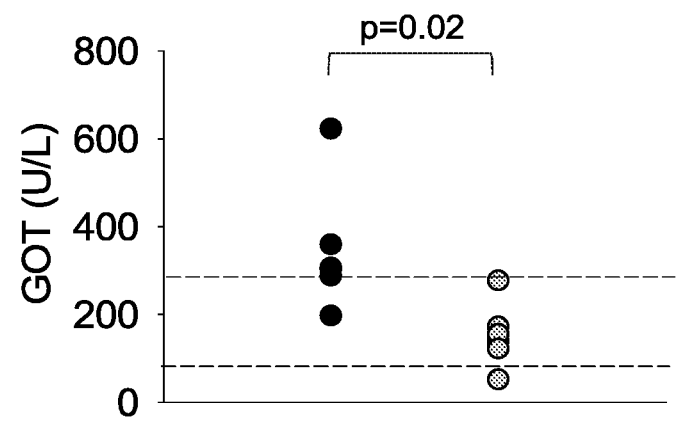
Figure 22:
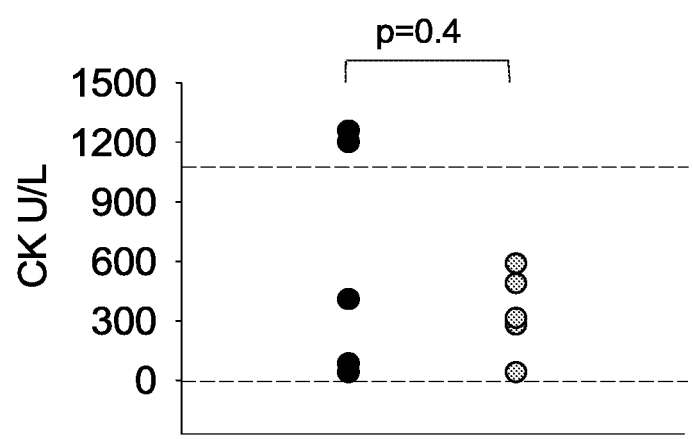
Figure 23:
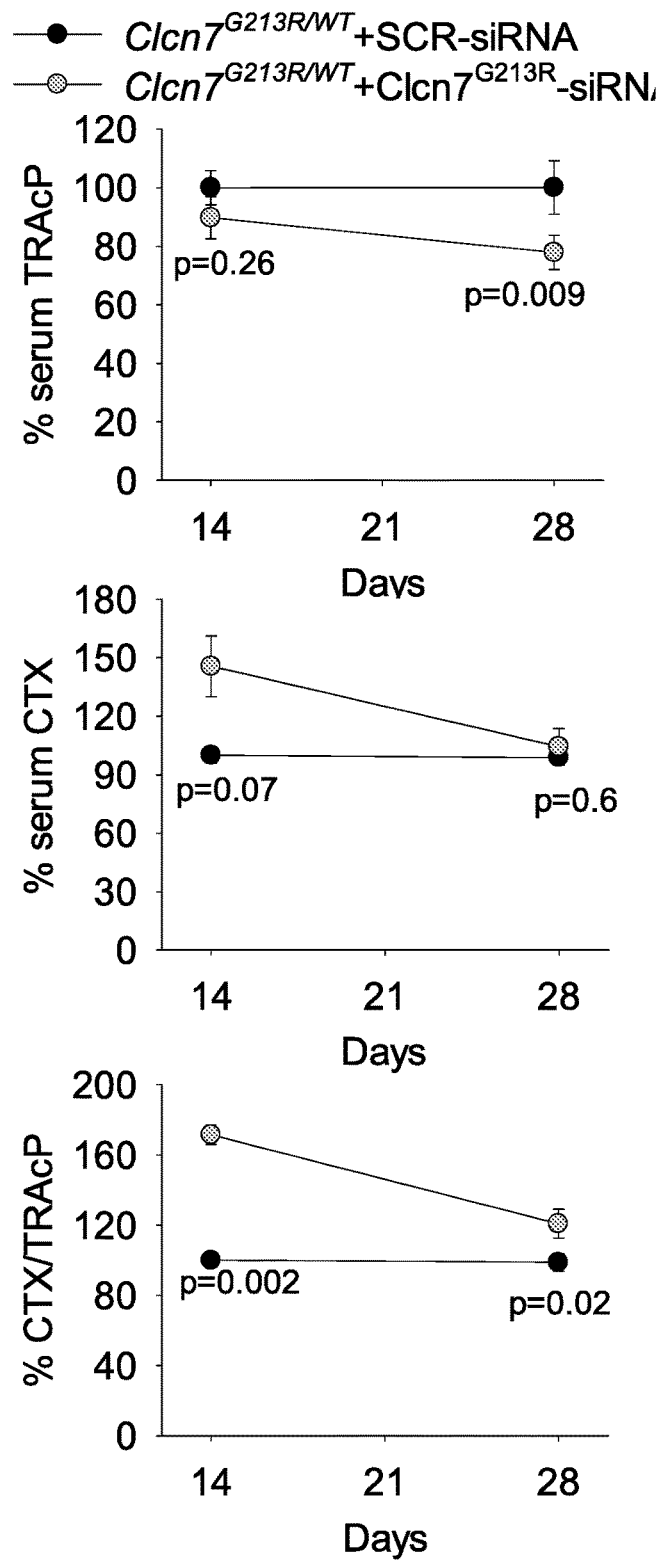
FIG. 23—WT and p.G213R KI mice received i.p. injections of 4 mg/kg of SRC-siRNA or p.G213R-clcn7 sticky siRNA/jetPEI, 3 times a week for 2 and 4 weeks. At the end of the experiment, mice were sacrificed and sera were collected for evaluating the levels of osteoclastic (isoform 5b of TRAcP enzyme) and bone resorption (CTX) biomarkers and for calculating the CTX/TRAcP ratio.
Figure 24:
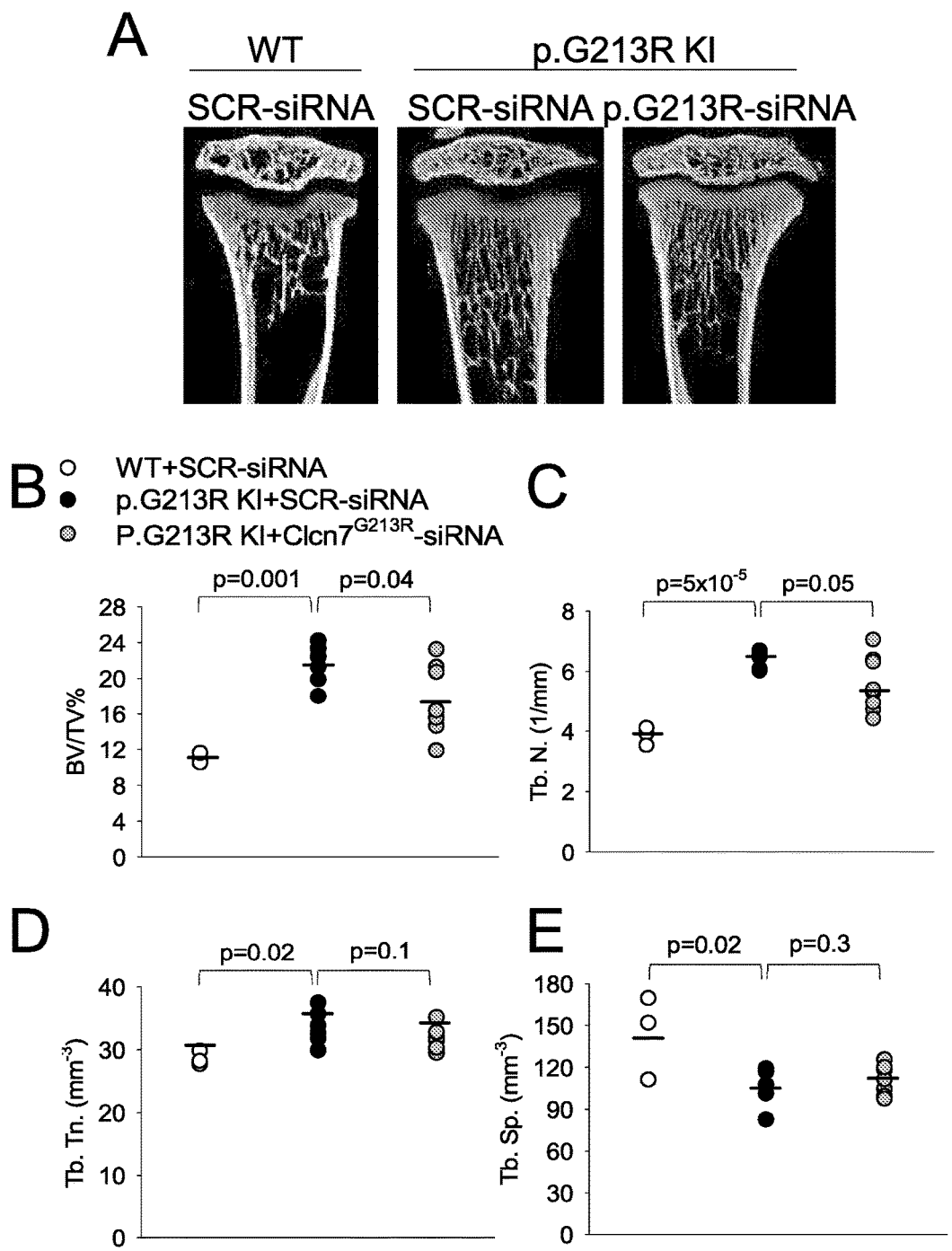
FIG. 24—Analysis of the bone phenotype of mice treated for 2 weeks as indicated in FIG. 22. (A) µCT analysis of the proximal region of the tibia. (B) trabecular bone volume over total tissue volume (BV/TV), (C) Trabecular number (Th.N). (D) Trabecular thickness (Tb.Th). (E) Trabecular separation (Tb.Sp). Mean±s.d. of 4-7 mice/group (Student's t test).
Figure 25:
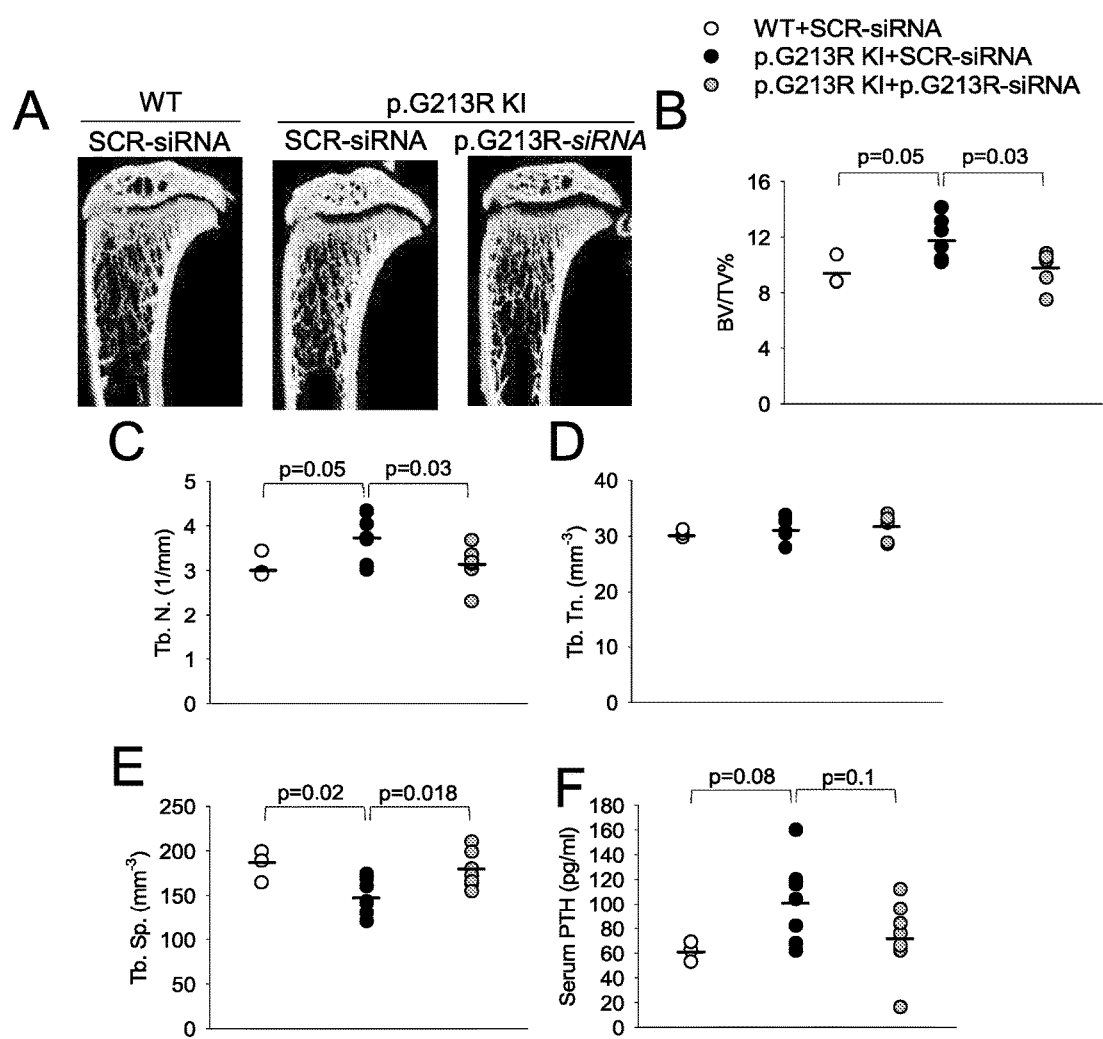
FIG. 25—Ten day-old WT and p.G213r KI mice received i.p. injections of 4 mg/kg of SRC-siRNA or of p.G213R-clcn7 sticky siRNA/jetPEI, 3 times a week for 4 weeks. At the end of the experiment mice were sacrificed and their bone phenotype analyzed. (A) µCT of the proximal region of the tibia. (B) Trabecular bone volume over total tissue volume (BV/TV). (C) Trabecular number (Tb.N). (D) Trabecular thickness (Tb.Th). (E) Trabecular separation (Tb.Sp). (F) Serum concentration of parathyroid hormone (PTH).
Figure 26:
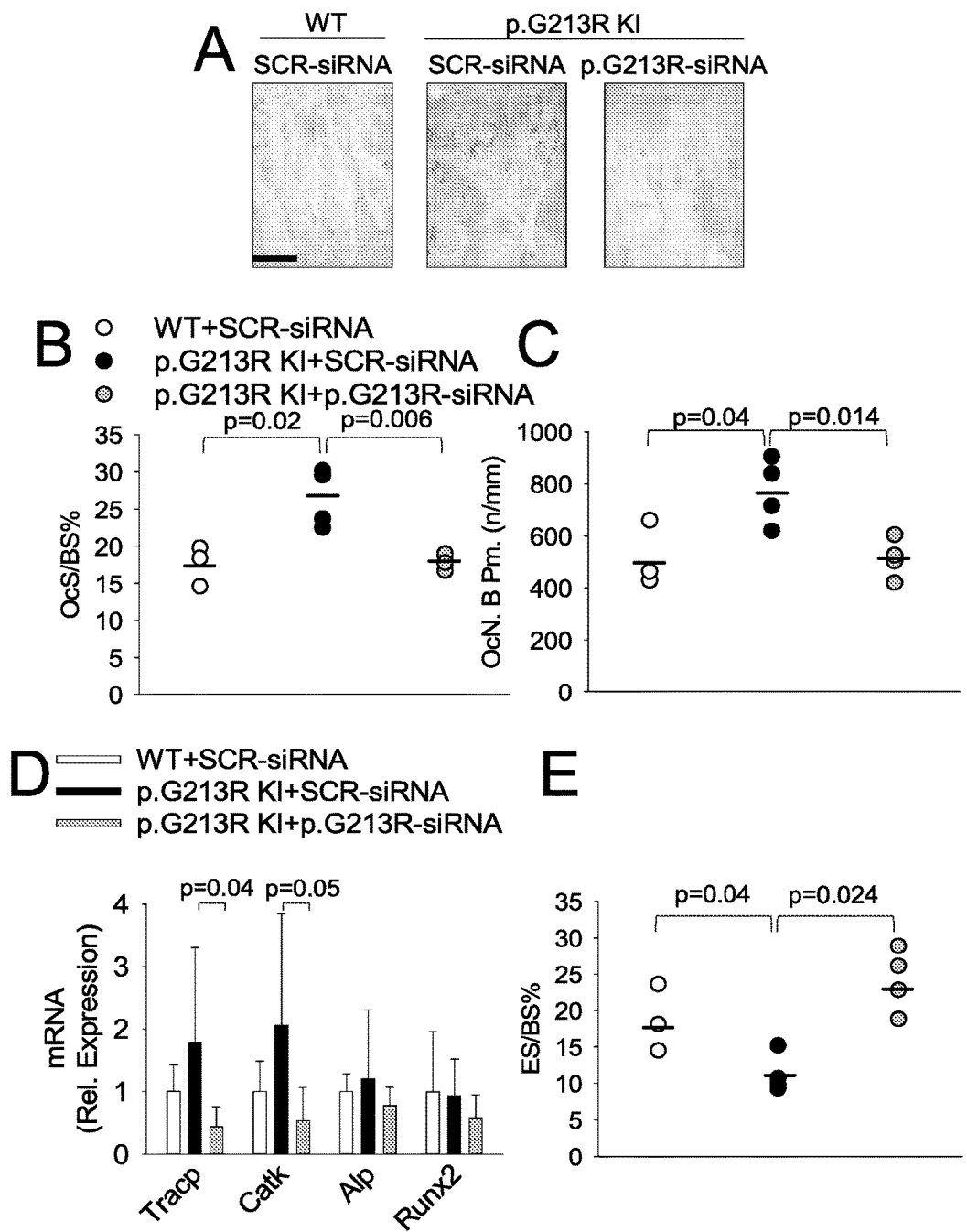
FIG. 26—Analysis of osteoclastic phenotype in mice described in FIG. 24. (A) Histochemical TRAcP enzyme staining to highlight osteoclasts (purple cells). Bar=100 µm. (B) Osteoclast surface over bone surface (Oc.S/BS). (C) Osteoclast number over bone perimeter (Oc.N/B Pm). (D) Transcriptional expression, by real-time RT-PCR on RNA extracted from the femurs, of osteoclast [Tracp and Cathepsin K (CatK)] and osteoblast [Alkaline phosphatase (ALP) and Runt-related transcription factor 2 (Runx 2)] genes normalized with gapdh. (E) Osteoclast-eroded surface over total bone surface (ES/BS). Mean±s.d. (Student's t test).
Figure 27:
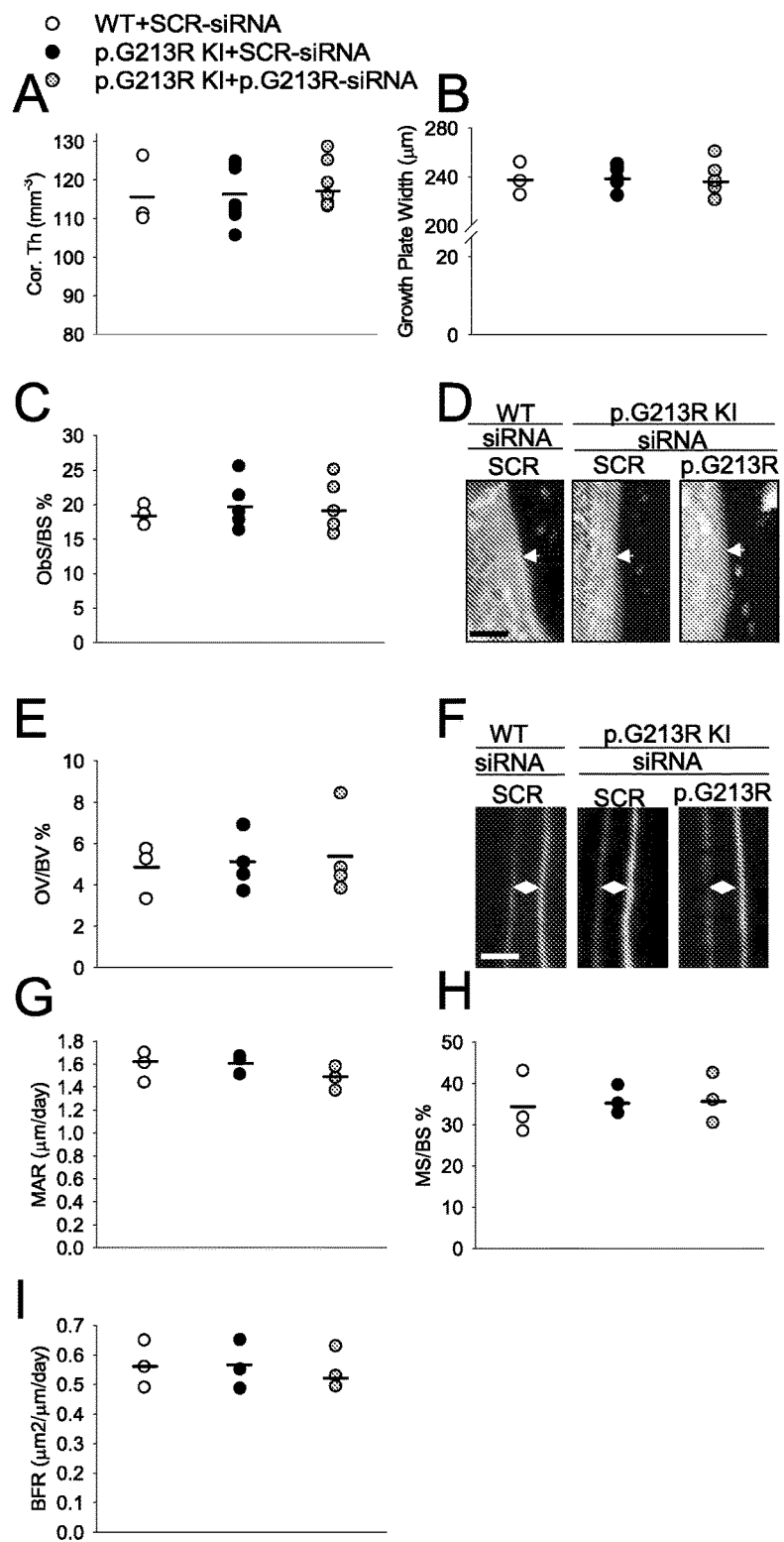
FIG. 27—Analysis of cortical, cartilagineous and osteoblastic parameters in mice described in FIG. 24. (A) Cortical bone thickness (Cor.Th). (B) Growth plate thickness (width). (C) Osteoblast surface over bone surface (Ob.S/BS). (D) Histological images of osteoid (arrows). Bar=5 µm. (E) Osteoid volume over bone volume (OV/BV). (F) Calcein labeling (green fluorescence) of mineral deposition (double arrowheads). Bar=2 µm. (G) Mineral apposition rate (MAR). (H) Mineralized surface over bone surface (MS/BS). (I) Bone formation rate (BFR).

To verify whether this treatment might have an effect on bone resorption in vivo, 10 day-old p.G213R-clcn7 ADO2 mice were treated, 3 times a week for 2 weeks and 4 weeks, with 4 mg/Kg of body weight of control (scrambled) sticky siRNA/jetPEI, or p.G213R-clcn7-specific siRNA. The treatment was well-tolerated and did not induce histopathological damages to vital organs (FIG. 21). Moreover, it improved renal, hepatic and muscle damage biomarkers (FIG. 22). The therapeutic effect of the treatment was analyzed on bone resorption biomarker CTX, normalized for osteoclastic biomarker TRAcP. The results demonstrated a significant increase of CTX serum levels and of the CTX/TRAcP ratio in mice treated with p.G213R-clcn7 sticky siRNA/jetPEI, as evidence of occurred activation of osteoclastic bone resorption (FIG. 23). Consistently, µCT analysis of the proximal end of the tibia showed a reduction of the trabecular bone volume/total tissue volume percentage and an improvement of structural trabecular variables already after 2 weeks of treatment (FIG. 24). After 4 weeks, total restoration of structural parameters (FIG. 25) and osteoclast functionality (FIG. 26) were witnessed, without any undesired effect on osteoblastic parameters (FIG. 27). Finally, an improvement also of biomechanic parameters was witnessed (FIG. 28), indicative of restoration of a good bone tissue quality. These results indicate that the bone resorption increase induced by the treatment of the Inventors was effective in correcting the bone phenotype of ADO2 mice.

To complete the therapeutic study, the ability of the identified siRNAs in reducing human mutated CLCN7 expression in osteoclasts from healthy donors transfected with the constructs carrying the mutations p.G215R, p.R286W and p. R767W, as well as the ability of the p.G215R-specific siRNA to improve bone resorption in osteoclasts obtained from a patient (FIG. 29) were further confirmed.

As to the siRNAs for the p. R767W mutation and for any other mutation to be analyzed in vivo, at present it cannot be suggested that murine models may be generated for each mutation, considering both the times and costs of implementation. Therefore, to test the in vivo efficacy of p.R767W siRNA 2C, which the Inventors had found to be active in vitro, an alternative strategy was adopted. Human breast cancer MDA-MB-231 cells were stably transfected with p.R767W-CLCN7/EGFP-C1 vector and treated in vitro with R767W siRNA 2C to verify its efficacy and specificity on the silencing of CLCN7 mutated mRNA (FIG. 30A). Then, the cells transfected with the p.R767W-CLCN7/EGFP-C1 vector were injected in the subcutaneous tissue of athymic (immunocompromised) Balb/c nu/nu mice, in which they formed macroscopically evident tumors. When the tumors reached the volume of 1 cm$^3$, the mice were treated with a single intraperitoneal injection of 4 mg/Kg of body weight of R767W 2C/jetPEI siRNA. After 48 hours mice were sacrificed, tumors were excided and analyzed, by real-time RT-PCR, for the expression of the EGFP transcript conjugated to the mutated gene. Under these experimental conditions, a tumor-expressed p.R767W-CLCN7/EGFP transcriptional reduction of about 50% was obtained. To check the specificity of the siRNA contrived by the Inventors, the same treatment protocol was carried out also by using siRNA for the WT CLCN7 gene, finding no change of transcriptional expression of the EGFP conjugated with the mutated construct (FIG. 30).

REFERENCE

1. Deng Y, Wang C C, Choy K W, Du Q, Chen J, Wang Q, Chung T K, Tang T. Therapeutic potentials of gene silencing by RNA interference: Principles, challenges, and new strategies. Gene. 538:217-227, 2014.
2. J. Bollerslev. Osteopetrosis, A genetic and epidemiological study, Clin. Genet. 31:86-90, 1987.
3. O. D. Bénichou, J. D. Laredo, M. C. de Vernejoul, Type II autosomal dominant osteopetrosis (Albers-Schönberg disease): clinical and radiological manifestations in 42 patients. Bone 26 (2000) 87-93.
4. A. Frattini, A. Pangrazio, L. Susani, C. Sobacchi, M. Mirolo, M. Abinun, M. Andolina, A. Flanagan, E. M. Horwitz, E. Mihci, L. D. Notarangelo, U. Ramenghi, A. Teti, J. Van Hove, D. Vujic, T. Young, A. Albertini, P. J. Orchard, P. Vezzoni, A. Villa, Chloride channel ClCN7 mutations are responsible for severe recessive, dominant, and intermediate osteopetrosis. J. Bone Miner. Res. 18:1740-1747, 2003.
5. B. Peruzzi, A. Teti. The physiology and pathophysiology of the osteoclast. Clin Rew Bone Miner Metab. 10:71-97, 2012.
6. A. Del Fattore, B. Peruzzi, N. Rucci, I. Recchia, A. Cappariello, M. Longo, D. Fortunati, P. Ballanti, M. Iacobini, M. Luciani, R. Devito, R. Pinto, M. Caniglia, E. Lanino, C. Messina, S. Cesaro, C. Letizia, G. Bianchini, H. Fryssira, P. Grabowski, N. Shaw, N. Bishop, D. Hughes, R. P. Kapur, H. K. Datta, A. Taranta, R. Fornari, S. Migliaccio, A. Teti. Clinical, genetic, and cellular analysis of 49 osteopetrotic patients: implications for diagnosis and treatment, J. Med. Genet. 43:315-325, 2006.
7. K. Chu, D. L. Koller, R. Snyder, T. Fishburn, D. Lai, S. G. Waguespack, T. Foroud, M. J. Econs. Analysis of variation in expression of autosomal dominant osteopetrosis type 2: searching for modifier genes, Bone 37:655-661, 2005.
8. E. Cleiren, O. Bénichou, E. Van Hul, J. Gram, J. Bollerslev, F. R. Singer, K. Beaverson, A. Aledo, M. P. Whyte, T. Yoneyama, M. C. deVernejoul, W. Van Hul, Albers-Schönberg disease (autosomal dominant osteopetrosis, type II) results from mutations in the ClCN7 chloride channel gene, Hum. Mol. Genet. 10:2861-2867, 2001.
9. U. Kornak, D. Kasper, M. R. Bösl, E. Kaiser, M. Schweizer, A. Schulz, W. Friedrich, G. Delling, T. J. Jentsch, Loss of the ClC-7 chloride channel leads to osteopetrosis in mice and man. Cell: 104:205-215, 2001.
10. A. Del Fattore, M. Capannolo, N. Rucci, A. Teti. New experimental therapeutic approach by siRNA for autosomal dominant osteopetrosis (ADO). Bone 46:142, 2010 (abstract).
11. Y. Ohnishi, Y. Tamura, M. Yoshida, K. Tokunaga, H. Hohjoh H. Enhancement of allele discrimination by introduction of nucleotide mismatches into siRNA in allele-specific gene silencing by RNAi. PLoS ONE. 3:e2248, 2008.
12. I. Alam, A. K. Gray, K. Chu, S. Ichikawa, K. S. Mohammad, M. Capannolo, M. Capulli, A. Maurizi, M. Muraca, A. Teti, M. J. Econs, A. Del Fattore. Generation of the first autosomal dominant osteopetrosis type II (ADO2) disease models. Bone. 59:66-75, 2014.

The invention claimed is:

1. A small interfering RNA (siRNA) 15 to 25 nucleotides in length that is complementary to a region comprising a point mutation in the messenger RNA (mRNA) of a mutated human gene CLCN7, wherein the CLCN7 point mutation is selected from the group consisting of: p.Y99C, p.D145G, p.W179X, p.G203D, p.L213F, p.G215R, p.P249L, p.R286W, p.R286Q, p.P470Q, p.R409W, p.L490F, p.G677V, p.688del, p.K689E, p.R762L, p.G765B, p.L766P, p.R767W, p.A788D, R223$X^1$ (wherein $X^1$ is L, P, G, K, W, I, M, C, or S), R265$X^1$, R271$X^1$, R280$X^1$, R281$X^1$, R286$X^1$, R326$X^1$, R362$X^1$, R403$X^1$, R405$X^1$, R409$X^1$, R436$X^1$, R526$X^1$, C211$X^2$ (wherein $X^2$ is F, S, Y, R, G, or W), C411$X^2$, C438$X^2$, W541$X^3$ (wherein $X^3$ is R, S, L, or G), W616$X^3$, L224$X^4$ (wherein $X^4$ is S, P, W, H, Q, R, F, I, M, or V), L227$X^4$, L564$X^4$, S290$X^5$ (wherein $X^5$ is Y, C, W, F, P, L, T, A, or N) S365X$^5$, S473X$^5$, G241X$^6$ (wherein X$^6$ is R, S, W, C, D, E, A, V), G347X$^6$, and G361X$^6$;

wherein the siRNA reduces the expression of the mutated ClC-7 protein.

2. The small interfering RNA (siRNA), according to claim 1, characterized in that the sequence of the siRNA comprises, in addition to the mutated nucleotide, one or more nucleotide mismatches compared to the corresponding target sequence of the mRNA containing the mutation.

3. The small interfering RNA (siRNA), according to claim 1, characterized in that the sequence of the siRNA comprises a short sequence dTdT or dAdT protruding to the 3' end.

4. The small interfering RNA (siRNA), according to claim 1, characterized in that the derivative is a siRNA comprising one or more chemically modified nucleotides, preferably selected from the group consisting of: 2'-alcoxy derivatives, 2'-methoxy-derivatives, 2'-ethoxy-derivatives, 2'-fluorine-derivatives, 2'-O-(2-methoxyethyl)-derivatives, 2'-O-benzyl-derivatives, 2'-O-methyl-4-pyridinil-derivatives, 2'-amino-derivatives, 2'-aminoethyl-derivatives, 2'-guanidinopropyl-derivatives, and LNAs-derivatives.

5. The small interfering RNA (siRNA), according to claim 2, characterized in that the derivative is a siRNA comprising one or more chemically modified nucleotides, preferably selected from the group consisting of: 2'-alcoxy derivatives, 2'-methoxy-derivatives, 2'-ethoxy-derivatives, 2'-fluorine-derivatives, 2'-O-(2-methoxyethyl)-derivatives, 2'-O-benzyl-derivatives, 2'-O-methyl-4-pyridinil-derivatives, 2'-amino-derivatives, 2'-aminoethyl-derivatives, 2'-guanidinopropyl-derivatives, and LNAs-derivatives.

6. The small interfering RNA (siRNA), according to claim 1, which is bonded or associated or complexed to polyethyleneimine (PEI), or to a derivative thereof selected from polyethyleneimine-polyethylene-glycol-N-acetylgalactosamine (PEI-PEG-GAL) complex, or polyethyleneimine-polyethylene glycol-tri-N-acetyl galactosamine (PEI-PEG-triGAL) complex.

7. The small interfering RNA (siRNA), according to claim 2, which is bonded or associated or complexed to polyethyleneimine (PEI) or to a derivative thereof selected from polyethyleneimine-polyethylene-glycol-N-acetylgalactosamine (PEI-PEG-GAL) complex, or polyethyleneimine-polyethylene glycol-tri-N-acetyl galactosamine (PEI-PEG-triGAL) complex.

8. The small interfering RNA (siRNA), according to claim 1, characterized in that the precursor is an shRNA.

9. The small interfering RNA (siRNA), according to claim 2, characterized in that the precursor is an shRNA.

10. The small interfering RNA (siRNA) according to claim 1 selected from the group consisting of:

```
                          (SEQ ID NO: 11)
CAACAGGGUGAAGAUCCCC, (SEQ ID NO: 13)
AACAGGGUGAAGAUCCCC, (SEQ ID NO: 14)
CCUGGGCCUGUGGCACCUG, (SEQ ID NO: 15)
CCUGGGCCUGUGGCACCUU, (SEQ ID NO: 16)
CCUGGGCCUGUGGCGCCUG, (SEQ ID NO: 17)
CCUGGGCCUGUGGCAUCUG, (SEQ ID NO: 19)
ACAGAGAAGUGGGACUUCU, (SEQ ID NO: 20)
ACAGAGAAGUGGGGCUUCG, (SEQ ID NO: 21)
ACAGAGAAGUGGGAUUUCG, (SEQ ID NO: 29)
GGAACUCGACAGGUACCGC,
``` all sequences optionally having a short dTdT or dAdT sequence protruding to the 3' end.

11. A method for therapeutic treatment of osteopetrosis comprising administering the small interfering RNA (siRNA), according to claim 1, to a subject in need thereof.

12. The method for therapeutic treatment according to claim 11, wherein the osteopetrosis is ADO2 caused by a mutation of the gene CLCN7.

13. The method for therapeutic treatment according to claim 11, wherein the therapeutic treatment provides for daily administration, or administration every 2, 3, 4, 5, 6 or 7 days; preferably with dosages for single administration from about 1 ng/kg of body weight to about 100 mg/kg of body weight, or from about 1 μg/Kg to 20 mg/Kg of body weight, or from about 1 mg/Kg to about 10 mg/Kg.

14. The method for therapeutic treatment according to claim 11, wherein the therapeutic treatment provides for intravenous, intraperitoneal, intramuscular, intradermal, subcutaneous, intraosseus, intracartilagineous, intraarticular, oral, oral with buccal dissolution, oral with sublingual dissolution, rectal, vaginal, intrabronchial, or inhalation administration; or for administration through electroporation, ultrasound-induced poration, cationic liposome-mediated transfection, microinjection, or electropulsation; or through viral or non-viral vectors; or through DNA encoding the siRNA; or as isolated (naked) RNA; or through three-dimensional, biocompatible matrices or implants.

15. The method for therapeutic treatment according to claim 11, wherein the siRNA is bonded or associated or complexed to polyethyleneimine (PEI), or to a derivative thereof selected from polyethyleneimine-polyethylene glycol-N-acetylgalactosamine (PEI-PEG-GAL) complex, or polyethyleneimine-polyethylene glycol-tri-N-acetyl galactosamine (PEI-PEG-triGAL) complex.

16. The method for therapeutic treatment according to claim 11, wherein the therapeutic treatment provides for administration of siRNA associated with one or more additional active principles.

17. A method for preparation of the siRNA according to claim 1, characterized in that the siRNAs have been prepared by chemical synthesis and subsequent purification.

18. A pharmaceutical composition comprising, as active ingredient, one or more small interfering RNA (siRNA), according to claim 1, optionally in combination with an additional active principle, and a pharmacologically acceptable excipient.

19. A pharmaceutical composition comprising, as active ingredient, one or more small interfering RNA (siRNA), according to claim 2, optionally in combination with an additional active principle and a pharmacologically acceptable excipient.

20. The pharmaceutical composition according to claim 18, which further comprises exosomes, liposomes, vesicles, or micelles.

21. The pharmaceutical composition according to claim 19, which further comprises exosomes, liposomes, vesicles, or micelles.

22. A method of therapeutic treatment of osteopetrosis comprising administering the pharmaceutical composition according to claim 18 to a subject in need thereof, preferably wherein the osteopetrosis is ADO2 caused by a mutation of the gene CLCN7.

23. A method of therapeutic treatment of osteopetrosis comprising administering the pharmaceutical composition according to claim 19 to a subject in need thereof, preferably wherein the osteopetrosis is ADO2 caused by a mutation of the gene CLCN7.

24. A small interfering RNA (siRNA) 15 to 25 nucleotides in length that is complementary to a region comprising a point mutation in the messenger RNA (mRNA) of a mutated human gene CLCN7 wherein the CLCN7 point mutation is selected from the group consisting of: G215R, G203D, G765B, G241$X^6$ (wherein $X^6$ is R, S, W, C, D, E, A, or V), G347$X^6$, G361$X^6$, G677V, and A788D;
   wherein the substitution causes a change in polarity; and
   wherein the siRNA reduces the expression of the mutated ClC-7 protein.

25. A small interfering RNA (siRNA) 15 to 25 nucleotides in length that is complementary to a region comprising a point mutation in the messenger RNA (mRNA) of a mutated human gene CLCN7 wherein the CLCN7 point mutation is selected from the group consisting of: W179X, W541$X^3$ (wherein $X^3$ is R, S, L, or G), W616$X^3$, and Y99C;
   wherein the substitution causes the loss of an aromatic ring; and
   wherein the siRNA reduces the expression of the mutated ClC-7 protein.

26. A small interfering RNA (siRNA) 15 to 25 nucleotides in length that is complementary to a region comprising a point mutation in the messenger RNA (mRNA) of a mutated human gene CLCN7 wherein the CLCN7 point mutation is selected from the group consisting of: R286W, R767W, R762W, R286Q, R223$X^1$, R265$X^1$, R271$X^1$, R280$X^1$, R281$X^1$, R286$X^1$, R326$X^1$, R362$X^1$, R361S, R403$X^1$, R405$X^1$, R409$X^1$, R436$X^1$, R526$X^1$, and K689E,
   wherein all lead to substitution of a basic amino acid that changes net charge; and
   wherein the siRNA reduces the expression of the mutated ClC-7 protein.

27. A small interfering RNA (siRNA) 15 to 25 nucleotides in length that is complementary to a region comprising a point mutation in the messenger RNA (mRNA) of a mutated human gene CLCN7 wherein the CLCN7 point mutation is selected from the group consisting of: C211$X^2$ (wherein $X^2$ is F, S, Y, R, G or W), C411$X^2$, and C438$X^2$;
   wherein the substitution results in the loss of disulfide bonds; and
   wherein the siRNA reduces the expression of the mutated ClC-7 protein.

28. A small interfering RNA (siRNA) 15 to 25 nucleotides in length that is complementary to a region comprising a point mutation in the messenger RNA (mRNA) of a mutated human gene CLCN7 wherein the CLCN7 point mutation is selected from the group consisting of: L224$X^4$ (wherein $X^4$ is S, H, Q, R, or H), L227$X^4$, L564$X^4$, P470Q, S290$X^5$ (wherein $X^5$ is W, F, P, L, or A), S365$X^5$, S473$X^5$, and D145G;
   wherein the substitution leads to the exchange of a hydrophobic for a hydrophilic amino acid; and
   wherein the siRNA reduces the expression of the mutated ClC-7 protein.

* * * * *